United States Patent [19]
Bierschenk et al.

[11] Patent Number: 5,674,949
[45] Date of Patent: *Oct. 7, 1997

[54] LIQUID-PHASE FLUORINATION

[75] Inventors: Thomas R. Bierschenk; Timothy Juhlke, both of Round Rock; Hajimu Kawa; Richard J. Lagow, both of Austin, all of Tex.

[73] Assignee: Exfluor Research Corporation, Round Rock, Tex.

[*] Notice: The term of this patent shall not extend beyond the expiration date of Pat. No. 5,322,903.

[21] Appl. No.: 466,798

[22] Filed: Jun. 6, 1995

Related U.S. Application Data

[63] Continuation of Ser. No. 240,225, May 10, 1994, Pat. No. 5,571,870, which is a continuation of Ser. No. 823,836, Jan. 17, 1992, Pat. No. 5,322,903, which is a continuation of Ser. No. 414,119, Sep. 28, 1989, Pat. No. 5,093,432, which is a continuation-in-part of Ser. No. 250,376, Sep. 28, 1988, abandoned.

[51] Int. Cl.$^6$ .................... C07B 9/00; C07C 17/04; C07C 17/02; C07C 19/02
[52] U.S. Cl. .................... 525/331.6; 204/157.95; 204/157.96; 204/157.97; 204/158.1; 204/158.11; 525/356; 525/357; 525/409; 549/428; 549/504; 549/540; 549/550; 558/54; 560/227; 560/229; 562/101; 562/113; 562/603; 562/605
[58] Field of Search ............... 525/331.6, 356, 525/357, 409; 204/157.95, 157.96, 157.97, 158.1, 158.11; 549/428, 504, 540, 550; 558/54; 560/227, 229; 562/101, 113, 603, 605; 564/496, 510; 568/407, 419, 615, 683, 684, 842; 570/129, 134, 147

[56] References Cited

U.S. PATENT DOCUMENTS

| | | | |
|---|---|---|---|
| 2,186,916 | 1/1940 | Gaylor | 87/9 |
| 3,242,218 | 3/1966 | Miller | 260/615 |
| 3,415,847 | 12/1968 | Talbott | 260/340.7 |
| 3,455,954 | 7/1969 | Prager | 260/340.2 |
| 3,654,369 | 4/1972 | Esmay | 260/583 |
| 3,665,041 | 5/1972 | Sianesi et al. | 260/615 A |
| 3,897,502 | 7/1975 | Russell et al. | 260/614 F |
| 4,076,916 | 2/1978 | Lagow | 526/43 |
| 4,144,374 | 3/1979 | Lagow et al. | 428/334 |
| 4,523,039 | 6/1985 | Lagow et al. | 568/615 |
| 4,686,024 | 8/1987 | Scherer et al. | 204/157.95 |
| 4,754,085 | 6/1988 | Gervasutti et al. | 570/175 |
| 4,755,567 | 7/1988 | Bierschenk et al. | 525/409 |
| 4,943,595 | 7/1990 | Scherer et al. | 514/722 |
| 4,973,716 | 11/1990 | Calini et al. | 549/504 |
| 4,996,369 | 2/1991 | Kalota et al. | 568/615 |
| 5,076,949 | 12/1991 | Kalota et al. | 662/54 |
| 5,093,432 | 3/1992 | Bierschenk et al. | 525/331.6 |
| 5,120,459 | 6/1992 | Kalota et al. | 252/54 |
| 5,322,903 | 6/1994 | Bierchenk et al. | 525/331.6 |

FOREIGN PATENT DOCUMENTS

| | | |
|---|---|---|
| 018606 | 11/1980 | European Pat. Off. . |
| 269029 | 6/1988 | European Pat. Off. . |
| 332601 | 9/1989 | European Pat. Off. . |
| 344935 | 12/1989 | European Pat. Off. . |
| 646557 | 4/1995 | European Pat. Off. . |
| 87/02994 | 5/1987 | WIPO . |
| 90/06296 | 6/1990 | WIPO . |

OTHER PUBLICATIONS

Müller, E., ed., "Methoden der Organischen Chemie" [Methods of the Organic Chemistry], pp. 18–24, Georg Thieme Verlag, Stuttgart (1962).

Bockemuller, W. Ann. 506, 20–59 (1933), Chem.Abst. 1934, 118.

Persico, D.F. et al., "A General Synthesis for Symmetrical Highly Branched Perfluoro Ethers: A New Class of Oxygen Carriers," J. Org. Chem., 50:5156–5159 (1985).

Persico, D. F. et al., "Synthesis of Perfluoropolyethers via Hydrocarbon Polyesters: A New General Method," Am. Chem. Soc., 107:1197–1201 (1985).

Scherer et al., "Synthesis of Perfluorochemicals by Photofluorination in Solution Using 100% Fluorine," Prog. Clin. Biol. Res., 122:450–451 (Abstract) (1983).

Lin, W.–H. et al., "Synthesis of Perfluorotetraalkyl Orthocarbonates Using Elemental Fluorine," J. Org. Chem., 54:1990–1992 (1989).

Lagow, R.J. et al., "Direct Fluorination: A New Approach to Fluorine Chemistry", Progress in Inorganic Chemistry, 26:161–189, 195–210 (1979).

Scherer et al., "A New Synthetic Approach to Perfluorochemical Liquid Phase Photofluorination with Elemental Fluorine. Part I," J. Fluorine Chem., 50:47–65 (1990).

Aikman, "The Synthesis of Trifluoromethyl Compounds and Pendant Functionalized Fluoropolymers by Direct Fluorination and the Use of Radio Frequency Glow Discharge Plasmas," Dissertation, The University of Texas at Austin (Dec. 1981).

Primary Examiner—Frederick Krass
Attorney, Agent, or Firm—Hamilton, Brook, Smith & Reynolds, P.C.

[57] ABSTRACT

This invention pertains to a method for liquid-phase fluorination for perfluorination of a wide variety of hydrogen-containing compounds.

20 Claims, 2 Drawing Sheets

LIQUID-PHASE FLUORINATION

RELATED APPLICATION

This application is a Continuation Application of U.S. patent application Ser. No. 08/240,225, which was filed on May 10, 1994, which issued as U.S. Pat. No. 5,571,870 on Nov. 5, 1996, which is a Continuation Application of U.S. patent application Ser. No. 07/823,836, filed on Jan. 17, 1992, which issued as U.S. Pat. No. 5,322,903 on Jun. 21, 1994, which is a Continuation Application of U.S. patent application Ser. No. 07/414,119, filed on Sep. 28, 1989, which issued as U.S. Pat. No. 5,093,432 on Mar. 3, 1992, which is a Continuation-in-Part Application of U.S. patent application Ser. No. 07/250,376, filed on Sep. 28, 1988, now abandoned, wherein the teachings of all of the applications are incorporated by reference herein.

BACKGROUND OF THE INVENTION

Hydrocarbons can be converted to fluorocarbons in two commercially viable ways. Electrochemical fluorination (ECF) is widely used to fluorinate materials which are soluble and stable in liquid hydrogen fluoride (HF). Of among the classes of materials prepared in this manner, perfluorotertiary amines and perfluorosulfonic acids are best suited for the technique giving yields generally in excess of 70%. Other classes of compounds such as carboxylic acids and their derivatives can be fluorinated electrochemically; however, the yields are usually low and have a tendency to decline rapidly as the number of carbons in the molecule is increased. In general, a very low yield (less than 25%) will be obtained for any perfluorinated carboxylic acid containing over 12 carbon atoms.

A second widely used process for preparing perfluorocarbons involves contacting a hydrocarbon, in the gaseous form, with cobalt trifluoride. This technique, although narrow in applicability, works well for low molecular weight hydrocarbons, especially polyaromatic compounds which are sufficiently volatile to allow vaporization. Examples of materials which can be fluorinated in this manner include decalin, tetradecahydrophenanthrene, naphthalene, decane, dodecane, etc.

Russell et al. (U.S. Pat. No. 3,897,502) describe a process whereby one or several fluorine atoms can be added to a partially fluorinated low molecular weight hydrocarbon. The material to be treated is dissolved in an inert solvent through which dilute fluorine is bubbled at low temperatures (−10° C. to −30° C.). The resulting product is a partially fluorinated material which typically contains several additional fluorine atoms. Scherer et al. (U.S. Pat. No. 4,686,024) teach a method for perfluorinating low molecular weight partially fluorinated hydrocarbons. Highly fluorinated starting materials are slowly pumped into a fluorocarbon solvent over a 3 to 5 day period. As the organic material is being delivered, a large excess of pure fluorine gas is bubbled through the solvent (typically a 5 to 8 fold excess). An ultraviolet lamp is used to activate the fluorine to produce the products of interest. The yields reported generally range from 20% to 50% for materials which contain 3 to 5 hydrogens which must be replaced by fluorine. Calin: et at. (European Patent Application 269,029) describe a fluorination process in which a hydrogenated ether compound is reacted with $F_2$ diluted with an inert gas in a liquid phase, in the presence of an alkali metal fluoride.

SUMMARY OF THE INVENTION

This invention pertains to liquid phase fluorination for perfluorination of a vide variety of hydrogen-containing compounds. The fluorination is performed in a perhalogenated liquid medium, such as a perfluorocarbon medium, a perhalogenated chlorofluorocarbon medium or a perhalogenated chlorofluoroether. The hydrogen-containing compound is introduced into the medium while the medium is agitated so that the compound is dissolved or dispersed within the medium. Fluorine gas, diluted with an inert gas, is then introduced into the medium to fluorinate the hydrogen-containing compound. The fluorine is diluted so that it is below the flammable limits of the liquid medium (in fluorine). The fluorine is introduced in an amount in excess of the stoichiometric amount needed to replace all of the hydrogen atoms of the hydrogen-containing compound. The temperature is maintained above the melting point of the solvent, below the temperature at which fluorine reacts with the liquid and below the temperature in which fragmentation of the hydrogen-containing compound occurs. The fluorination is carried out in the absence of ultraviolet light and continued (as a batch or continuous process) until all the hydrogen-containing compound is introduced into the liquid medium and fluorinated.

It has been found, in accordance with the present invention, chat a vide variety of hydrogen-containing compounds can be fluorinated using the liquid phase fluorination. The method of the invention can be used to prepare fluorinated products which can be prepared by ECF and cobalt trifluoride processes as well as products such as perfluoropolyethers, high molecular weight fluorocarbon diacids, and high molecular weight hydrocarbons which cannot be prepared by the existing fluorination technologies. The fluorinated products can be obtained typically in higher yield and in purer form than in other processes.

The mild conditions employed in the method of this invention make it possible to preserve chemical functionalities on a fluorinated molecule. For example, chlorinated hydrocarbons can be converted to polyfluorinated materials with essentially all of the chlorine being retained in original positions. Polyesters and acyl fluorides can be converted to perfluorocarbons with essentially complete retention of the ester functionality. Perfluoro-tertiary amines, sulfonic acids, sulfonic esters and ketones can all be prepared in high yield.

DETAILED DESCRIPTION OF THE INVENTION

Figure 1:
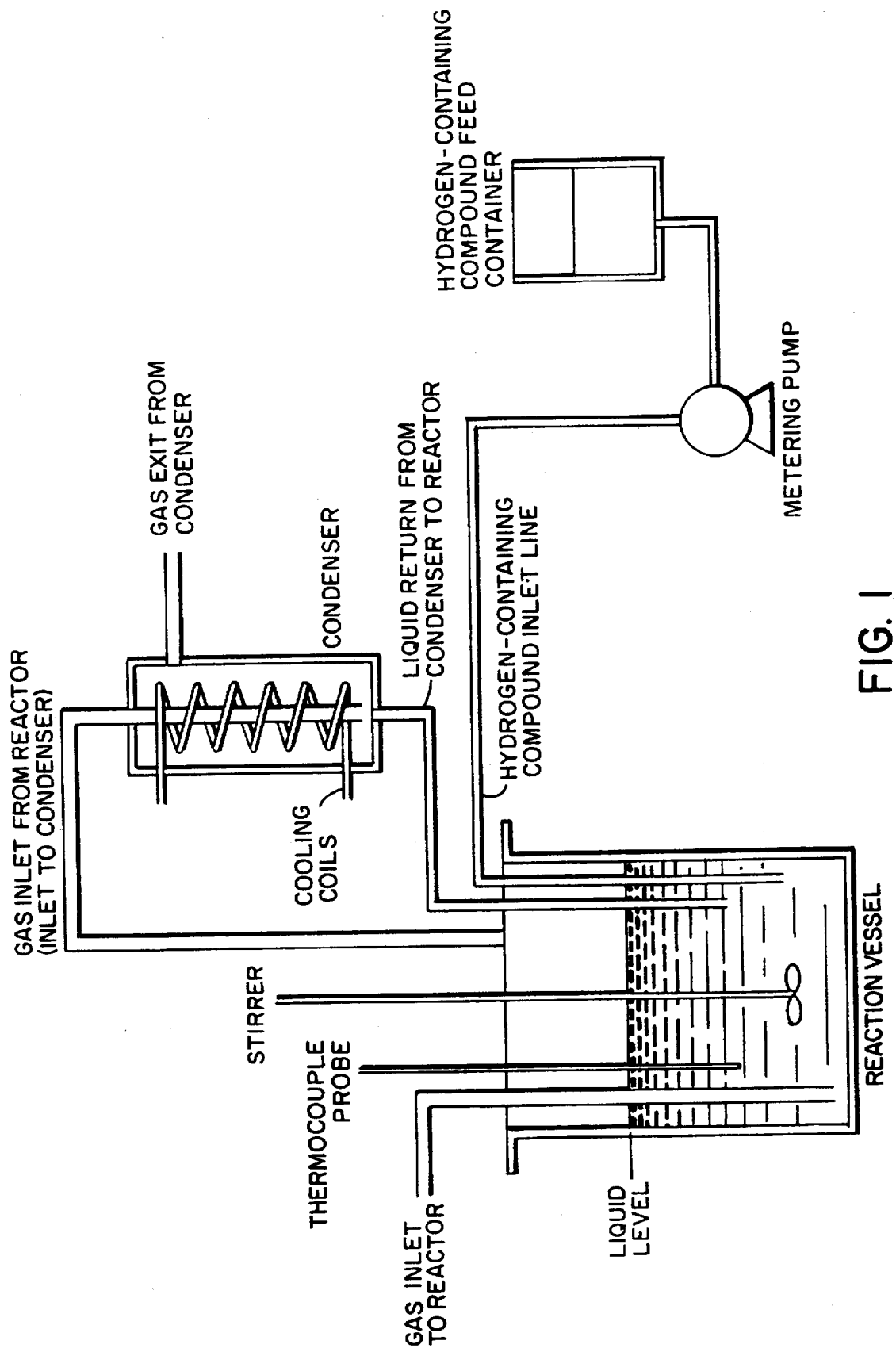
FIG. 1 is a schematic representation of a liquid phase fluorination reactor.

The perfluorination reactions are carried out in a liquid phase fluorination reactor. A suitable reactor is shown schematically in FIG. 1. The reactor consists of a reaction vessel equipped with a means for agitating vigorously a liquid contained therein (a stirrer), a means of removing the heat (internal or external cooling coils, a constant temperature bath, etc.), a fluorine inlet, an inlet line for introducing the hydrogen-containing compound to be fluorinated, a gas outlet line, a condensor for condensing vaporized liquid from the reaction vessel and a liquid return line for returning condensed liquid back into the reaction vessel. Downstream from the reactor a hydrogen fluoride scrubber (such as a sodium fluoride-filled tube), instrumentation for measuring the fluorine concentration in the off gas (which can be done titrametrically, with an ion specific electrode, calorimetrically, etc.) and a fluorine scrubber (such as a tube filled with alumina, sulfur, etc.) are installed.

Liquid perhalogenated chlorofluorocarbons, chlorofluoroethers and perfluorocarbons serve as useful liquid phase medium in the fluorination reaction. Collectively, these compounds are referred to herein as the perhalogenated liquid fluorination medium. Examples of some such chlorofluoroethers are:

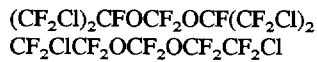

$CF_2ClCF_2OCF_2OCF_2CF_2Cl$

When perfluorinating low molecular weight polyethers, it is preferable that the liquid fluorination medium be the same as the fluorination product of the reaction. This eliminates the need to separate the fluorinated product from the liquid medium.

According to the method of the invention, the fluorination reaction is carried out by placing a perhalogenated liquid in the reactor, such as a perfluorocarbon, a perhalogenated chlorofluorocarbon or a perhalogenated chlorofluoroether. For clarity, the following description pertains to 1,1,2-trichlorotrifluoroethane which is a useful solvent for most reactions; however, as pointed out above, other perhalogenated chlorofluorocarbons or perfluorocarbons, such as Fluorinert FC-75 described in Example 70, may be used.

Before beginning the reaction, the reactor is purged of air, generally, by flushing the reactor with inert gas such as nitrogen gas for approximately 30 minutes. The reactor temperature is adjusted to the desired temperature, i.e. a temperature high enough for the fluorination reaction to occur but low enough to prevent fragmentation of the hydrogen-containing compound, usually between −40° C. and +150° C., preferably between −10° C. and +50° C. Similarly, the condensor is cooled to its operating temperature (typically −35° C). The hydrogen-containing material to be fluorinated is introduced into the reactor at a controlled rate as fluorine gas and a diluent inert gas (e.g. nitrogen), are introduced therein. Preferably, the fluorine is bubbled through the vigorously agitated perhalogenated liquid fluorination medium but it may also be introduced into the vapor space of the reactor. The fluorine is introduced at a rate slightly above that required to theoretically replace all of the hydrogen atoms present on the molecule to be fluorinated (typically a 10% to 40% excess of fluorine is used). The fluorination reaction is carried out in the absence of ultraviolet light.

Upon completing the addition of the hydrogen-containing material, the fluorine concentration in the gas exit line typically increases sharply, denoting the end of the fluorination reaction. However, in the case of high molecular weight polymers (5,000 to 30,000 amu) and hydrocarbons which are either insoluble or sparingly soluble in the liquid, it is often beneficial to slowly meter into the reactor a small amount of a low molecular weight hydrocarbon such as benzene after adding the hydrogen-containing compound to be fluorinated to ensure perfluorination. The hydrocarbon reacts with the fluorine producing an abundance of fluorine radicals which are highly reactive and replace the last remaining hydrogen atoms on the product.

The hydrogen-containing compound to be fluorinated can be metered into the reactor neat if it has a sufficiently low viscosity (less than about 50 cst. at 100° F.), or it may be diluted with a solvent. Normally, the solvent is the fluorination liquid. For example, if 1,1,2-trichlorotrifluoroethane is used as the liquid fluorination medium, the material to be fluorinated is typically diluted with 1,1,2-trichlorotrifluoroethane before being introduced into the reactor. With high molecular weight polymers which are often solids, the dilution becomes very important.

If the hydrogen-containing compound is insoluble in the perhalogenated liquid fluorination medium, it can still be fluorinated in high yield by forming an emulsion with the liquid fluorination medium. One convenient way of preparing such compounds involves preparing the emulsion continuously in situ as the fluorination reaction proceeds. For example, if 1,1,2-trichlorotrifluoroethane is used as the fluorination liquid, the hydrogen-containing compound is first diluted with a suitable solvent which has a high solvating power and at the same time will consume little if any of the fluorine. Chloroform, trichloroethene, trichloroethane, trifluoroacetic acid or trifluoroacetic anhydride can usually be used as the solvent. Upon dissolving the hydrogen-containing compound in the solvent, 1,1,2-trichlorotrifluoroethane is then added slowly until the reactant solution becomes cloudy, signifying that the hydrogen-containing compound is beginning to precipitate or become immiscible with the solvent mixture. The hydrogen-containing compound/1,1,2-trichlorotrifluoroethane/solvent mixture is then slowly pumped into the fluorination reactor in the usual manner, as previously described. As the solution contacts the perhalogenated liquid fluorination medium, a fine emulsion or precipitate is formed depending upon the nature of the hydrogen-containing compound. The solution, although heterogeneous, allows for fluorination as though it was homogeneous owing to the very small particle size of the suspended material.

The fluorine gas is diluted with an inert gas such as nitrogen. This is of particular importance if a fluorination medium such as 1,1,2-trichlorotrifluoroethane is used. It is imperative to keep the fluorine concentration low so that the perhalogenated liquid fluorination medium and fluorine in the vapor space do not form a flammable mixture. The flammability limits of various solvents in fluorine gas can be determined by spark testing. In a typical reaction, a fluorine concentration of 10 to 40% in 1,1,2-trichlorotrifluoroethane works well. If operating properly, the fluorine concentration in the exit gas will be between 2 and 4%.

The continuous addition reactor may be operated in a batch or continuous mode. If operating continuously, a small portion of the reactor contents is removed continuously or periodically. The product is recovered by distillation or other means and the liquid fluorination medium is returned to the reactor.

Sodium fluoride or other hydrogen fluoride scavengers, (see U.S. Pat. No. 4,755,567) may be present in the solution to scavenge the by-product hydrogen fluoride. The preferred mode for carrying out the reaction for many polyethers is with a sufficient quantity of sodium fluoride being present to complex with all of the hydrogen fluoride formed during the fluorination. When fluorinating ethers in the presence of sodium fluoride, improved yields are obtained while chain cleavage and rearrangements are minimized.

Polyethers containing sterically hindered oxygens and/or chlorine in the vicinity of the oxygen can be fluorinated in high yield without having a hydrogen fluoride scavenger present. Naturally, these reactions are more amenable to continuous processes than those reactions requiring a hydrogen fluoride scavenger.

The method of this invention is extremely versatile and allows fluorination of many different classes of hydrogen-containing materials, including ethers and polyethers having 5 to 10,000 carbon atoms. Cyclic ethers having more than 10 carbon atoms can also be fluorinated By the methods of this invention. To illustrate this, the fluorination of several classes of compounds is described below.

Production of Perfluorinated Acids and Their Derivatives.

Perfluorinated acids such as $C_7F_{15}COOH$ and their derivatives have received much attention through the last forty years principally because many products of commercial value such as oil- and water-repellant finishes for textile and paper, stain-repellant finishes for leather, surfactants for a variety of applications and other commercial products are based on perfluorinated acids and their derivatives. Perfluorinated acids are made primarily by two methods. The first method involves electrochemical fluorination (ECF) of acid derivatives to perfluorinated acid derivatives. The second main method involves the use of telomers made from perfluoroiodoalkanes and tetrafluoroethylene in multi-step routes. For a discussion of how perfluorinated acid derivatives are made see, for example, R. E. Banks, ed., *Preparation, Properties and Industrial Applications of Organofluorine Compounds*, Chapter 1, John Wiley & Sons, 1982.

In ECF of acid derivatives, the yield of perfluoro acid produced falls of rapidly with increasing chain length of the feed stock. The effect of molecular weight on the yield is best illustrated by the following reaction (1):

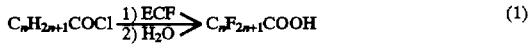

n-6, 16% yield; n-7, 10% yield; n-11, 0.5% yield. An important contributing factor for the low yields is the formation of cyclic perfluoropolyethers when n-3. For example, a major by-product of perfluorooctanoic acid production is perfluoro-(2-n-butyltetrahydrofuran). Other by-products include tars and fragmentation products. The formation of by-products in ECF reactions of acid derivatives makes it difficult if not impossible to make materials such as some of the long chain diacids described in the examples which follow.

With the liquid phase fluorination techniques of this invention, it is possible to make a wide variety of perfluorinated acids and acid derivatives in very high yields. In many cases there is practically no loss of functional groups and there are very few side reactions.

The hydrogen-containing starting material can be reacted with fluorine in a reactor such as the one just described and shown in the schematic of FIG. 1. There are a variety of acid derivatives that can be reacted. Organic acids themselves are generally not a good choice. For example, the fluorination of decanoic acid gives perfluorononane in high yield as the product decarboxylates during the fluorination. Although decanol can be used as a reactant to produce mainly perfluorodecanoic acid, a potential by-product of this reaction is a hypofluoride so it may not be the reactant of choice. Acid halides work very well as organic reactants. Using decanoyl fluoride, perfluorodecanoic acid can be made in high yields. However, when decanoyl chloride is used as the reactant, a considerable amount of chlorine substitution on the product results. With decanoyl chloride, the resulting product after hydrolysis contains a material where about 50% of the molecules have one or more chlorines in the molecule (i.e. $C_9F_{18}ClCOOH$). Another disadvantage of using acid halides is that they must be handled under anhydrous conditions as they will easily hydrolyze to form acids which decarboxylate during the fluorination. However, the use of acid fluorides might be the preferred feedstock choice in a production facility as the least amount of elemental fluorine is needed. For laboratory-scale reactions, esters are probably the reactant of choice. With primary esters, both ends of the ester group are converted to perfluoro acids after fluorination followed by hydrolysis. For example, the hydrolysis of one mole of perfluoro(octanoyl octanoate), gives two moles of perfluoro octanoic acid. Using octanoyl acetate, one mole of perfluorooctanoic acid and one mole of trifluoroacetic acid is made. As can be seen from the reactions below:

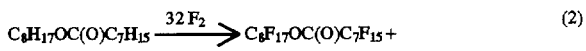

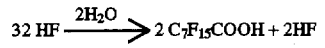

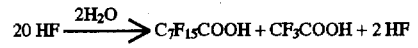

slightly more fluorine is required to fluorinate an ester than the corresponding acid fluoride to make the same product. However, the hydrocarbon esters are stable in air and can be handled in glass equipment. In a production facility, it may be more cost effective to use acid fluorides since the main cost of products would probably be associated with the cost of fluorine gas.

When secondary alcohols or esters of secondary alcohols are reacted using this invention, the resulting product after hydrolysis is a perfluoroketone. For example, the hydrolysis of perfluoro(isopropyl octanoate) yields perfluorooctanoic acid and hexafluoroacetone after hydrolysis. 2-Octanol yields perfluoro-2-octanone and acetyl-2-octanoate yields trifluoroacetic acid and perfluoro-2-octanone after hydrolysis. These reactions are shown as follows:

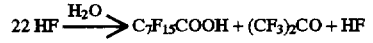

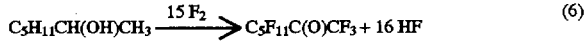

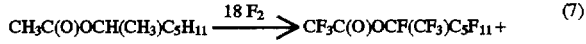

When tertiary alcohols are reacted according to this invention, tertiary alcohols are produced in low yields with mostly perfluoroalkanes being produced. However, esters of tertiary alcohols give fair yields of tertiary perfluoro alcohols after hydrolysis.

There are many applications in the aerospace and related industries, in which, o-rings, gaskets and sealants are needed which can withstand high temperatures while also exhibiting good low-temperature flexibility. The methylol-terminated prepolymers which can be made by reduction of perfluorocarbon diacids and described in several of the following examples are promising precursors for such materials. For example, polyurethanes can be prepared by reacting hydroxyl-terminated fluorocarbons with aromatic diisocyanates. Similarly, useful binders can be prepared by reacting the methylol-terminated fluorocarbon with paraformaldehyde.

Production of Perfluorinated Ethers

An important class of materials that can be produced using the liquid phase fluorination techniques of this invention are perfluoroethers and polyethers. The production of perfluoropolyethers by ECF or cobalt trifluoride fluorination has not resulted in commercially viable processes due to extensive fragmentation reactions which usually occur. Methods have been developed for making perfluoropolyethers by direct fluorination (see, for example, U.S. Pat. No.

3,775,489). Liquid-phase fluorination provides a process capable of producing better quality (e.g., higher linearity) perfluoropolyethers having higher yields.

Hydrocarbon ethers such as polyethers are more difficult to prepare by direct fluorination than other hydrocarbons due to their sensitivity to the by-product hydrogen fluoride generated in the process. Hydrogen fluoride has a tendency to cause acid cleavage of the ether linkages. The degree of sensitivity varies greatly with the structure of the ether. Linear polyethers containing a low carbon to oxygen ratio are most reactive while polyethers containing some chlorine and fluorine substituents are remarkably stable in the presence of hydrogen fluoride. In spite of this, virtually all ethers can be prepared by the method of this invention in excellent yields if provisions are taken to minimize the exposure of the ether to the hydrogen fluoride. A variety of techniques can be used to accomplish this. For example, sodium fluoride can be charged into the reactor along with the fluorination liquid. The sodium fluoride slurry scavenges the hydrogen fluoride to give sodium bifluoride.

Figure 2:
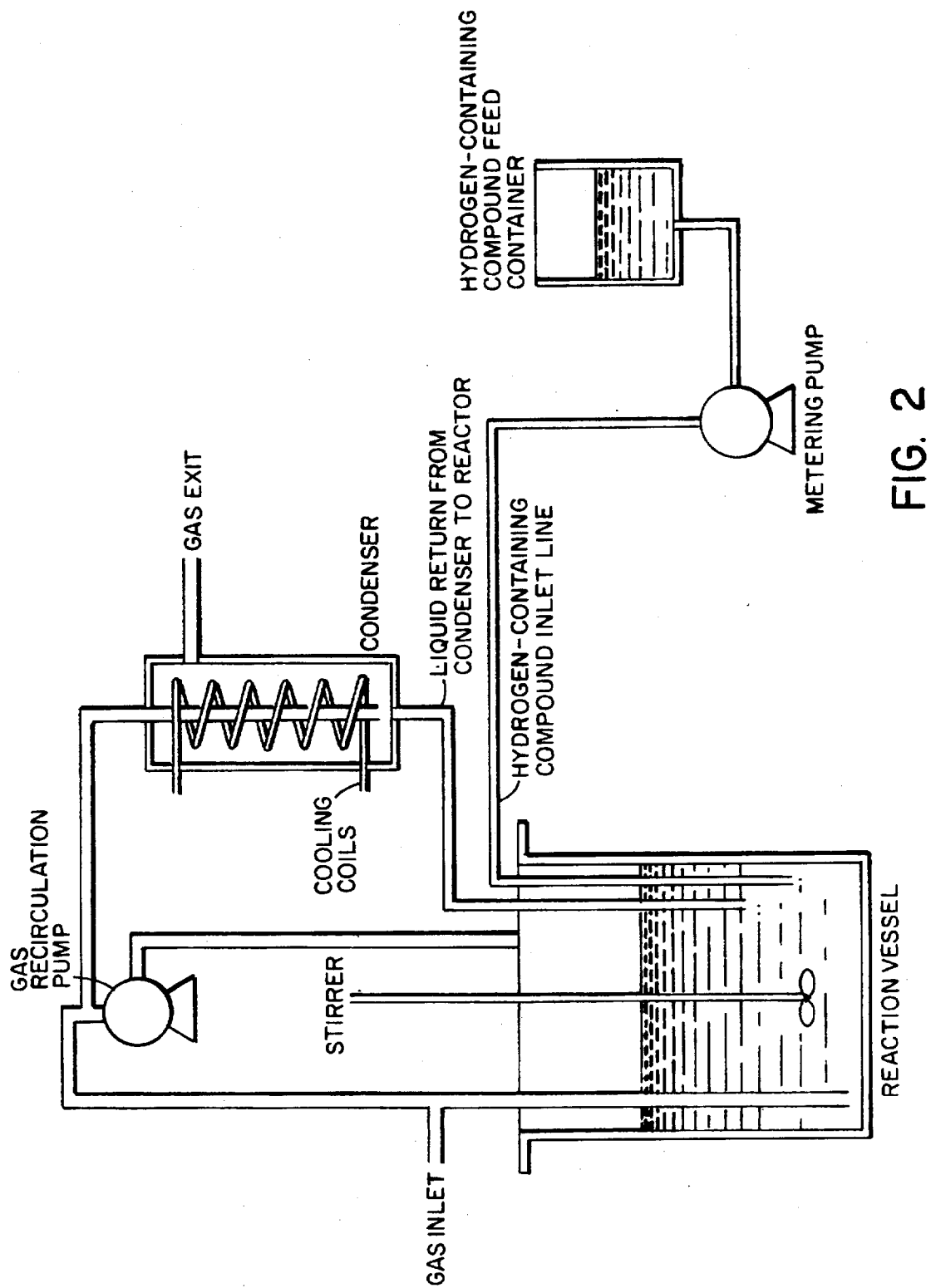
FIG. 2 is a schematic representation of another liquid phase fluorination reactor.

A slight modification of this approach which works well involves placing sodium fluoride pellets in a second vessel through which the gaseous products of the reaction are passed. For this approach, the reactor shown in FIG. 2 can be used. A gas pump is used to circulate the gases in the reactor through the sodium fluoride bed (which removes the hydrogen fluoride) and then to reinject the gases, which contain unreacted fluorine, back into the reactor. By isolating the sodium fluoride from the product, the recovery of the product is greatly simplified and the process can be made continuous by employing several sodium fluoride beds which can alternately be regenerated by heating.

An alternate approach which gives satisfactory results involves using a perhalogenated liquid fluorination medium with a boiling point high enough to allow the fluorination reaction to be carried out at a sufficiently high temperature to allow the by-product hydrogen fluoride to be quickly removed from the reactor. This greatly facilitates the removal of hydrogen fluoride because the solubility of hydrogen fluoride in the liquid phase decreases with increasing temperature. Typically, a perhalogenated liquid fluorination medium having a boiling point near 100° C. works well. Thus, it is often possible to prepare perfluoropolyethers in high yield without using a hydrogen fluoride scavenger.

A slight variation of this approach involves placing a sodium fluoride trap in the liquid return line between the condenser and the reactor. The majority of the hydrogen fluoride is swept from the reactor and is condensed in the condenser along with some of the fluorination liquid. The fluorination liquid is phase separated from the hydrogen fluoride and is returned to the reactor. By placing a sodium fluoride trap in the liquid return line, one can be certain that the liquid returning to the reactor is free of hydrogen fluoride.

Production of Other Fluorochemicals

There are a wide variety of other fluorochemicals that can be made using this invention. Classes of materials that can be fluorinated include alkanes, alkenes, aromatic hydrocarbons, sulfonic acid derivatives, amines, chlorinated hydrocarbons, carboxylic acid derivatives, ethers, formals, acetals, ketals, epoxides and others.

Perhalogenated acetals, ketals and formals are described in U.S. patent application Ser. No. 07/250,384, filed Sep. 28, 1988 now abandoned, and U.S. Pat. No. 5,053,536, issued to Bierschenk et al., Mar. 3, 1992. Perhalogenation of epoxides is described in U.S. patent application Ser. No. 07/251,135, filed Sep. 28, 1988 now abandoned and Ser. No. 07/414,134 now abandoned, filed concurrently herewith. The teachings of each of these applications are incorporated by reference herein.

Both large and small molecules can be reacted using this invention to yield products ranging from single compounds to polymers. Alkanes and alkenes are generally quite soluble in 1,1,2-trichlorotrifluoroethane and similar solvents so they can easily be added either neat or in solution to the reactor. Materials such as perfluorokerosene are useful as mass markers in mass spectrometry. It is also possible to produce unique materials such as elastomeric perfluoroethylene-propylene copolymers using this invention. Hydrocarbon ethylene-propylene copolymers can be produced with nearly any ratio of ethylene to propylene so it is possible to use this invention to produce perfluoroethylene-propylene copolymers with ethylene to propylene ratios of about one to one which are elastomeric. If one uses perfluoroethylene and perfluoropropylene monomers to produce perfluoroethylene-propylene copolymers, the difference in monomer reactivity limits the amount of hexafluoropropylene that can be incorporated in the polymer to a range such that the polymer is not elastomeric. Aromatic and polyaromatic hydrocarbons, such as phenanthrene or polystyrene, can also be reacted using this invention with the aromatic groups becoming saturated with fluorine as the hydrogens are being replaced with fluorine. Preferably, mono and polycyclic aromatic compounds will have 6 to 30 carbon atoms.

Perfluoroamines can be made using this invention as well. Although some of the yields are relatively low due to the tendency to form tars at some stage of the reaction, the addition of an acid such as trifluoroacetic acid to the hydrocarbon amine appears to improve the yield and the use of both a chlorofluorocarbon and liquid HF as the liquid phase in the reactor improves the yield even more.

Sulfonic acids and derivatives such as sulfonyl chlorides, sulfonyl fluorides and alkyl sulfonates can be converted in high yields to give perfluoroalkyl sulfonyl derivatives. Fluorocarbon sulfonyl derivatives offer many advantages over conventional hydrocarbon surfactants. They give lower surface tensions, are more stable, show surface activity in organic systems and exhibit both excellent water and oil repellancy. Although low molecular weight fluorocarbon sulfonic acid derivatives can be prepared in the electrochemical cell, the fluorination of hydrocarbon sulfonyl derivatives in perhalogenated liquid fluorination medium represents a superior means of preparing fluorocarbons having over six to eight carbons. Anionic surfactants based on fluorocarbon sulfonic acids function at increasingly lower concentrations as the molecular weight of the fluorocarbon chain in the surfactant increases.

The invention described is particularly advantageous for preparing fluorocarbons containing two or more sulfonic acid derivatives. Unlike the electrochemical cell which gives very poor results when fluorinating molecules containing more than one sulfonic acid derivative, materials such as these can be prepared in good to moderate yields using the liquid phase fluorination reactor.

This invention also relates to a method of preparing chlorofluorocarbons by the reaction of chlorinated organics with fluorine gas. The reaction takes place at temperatures low enough to replace essentially all of the hydrogen atoms with fluorine while retaining all of the chlorine atoms present in the molecule. For example, telomers of polyvinyl chloride (PVC) can be fluorinated to give telomers of chlorotrifluoroethylene which contain chlorine on every other carbon. The regular structure results because vinyl chloride reacts strictly in a head-to-tail fashion. In contrast, telomers of chlorotrifluoroethylene prepared by polymerizing chlorotrifluoroethylene have a random structure and, as a result, are considerably less stable in air and in the presence of metal surfaces. The telomers prepared by fluorination of polyvinyl chloride are presently being contemplated as nonflammable hydraulic fluids.

Similarly, telomers of vinylidene chloride can be fluorinated to yield chlorofluorocarbons having a regular structure as shown by Equation (8). These materials are also reasonably stable and do not contain chlorine on adjacent carbon atoms.

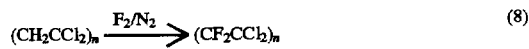
(8)

The invention is further illustrated by the following non-limiting examples:

EXAMPLE 1

A 10 liter stirred tank reactor was loaded with 5.0 liters 1,1,2-trichlorotrifluoroethane. Octanoyl octanoate (877 g) was placed in an erlenmeyer flask and diluted to about 1900 ml with 1,1,2-trichlorotrifluoroethane. The nitrogen flow was set at 3400 cc/min and the fluorine flow was set at 800 cc/min. After three minutes, the octanoyl octanoate solution was added at a rate of 13.7 grams octanoyl octnoate per hour or 0.5 ml per minute. The reactor temperature was maintained at 0° C. and the condenser temperature at −35° C. After all the octanoyl octanoate was added (64 hours), the nitrogen flow was reduced to 1500 cc/min and the fluorine was reduced to 300 cc/min. For 30 minutes these flows were maintained while 2 grams of benzene dissolved in 1,1,2-trichlorotrifluoroethane was added at a rate of 4 grams per hour of benzene. After 30 minutes of benzene addition, the benzene flow was stopped. Fifteen minutes after the benzene flow was stopped, the fluorine was turned off. After purging with nitrogen. 300 grams technical grade methanol was added to the reactor. Approximately seven liters of material was dumped from the reactor which was distilled to yield 2430 grams that boiled at 155° C. Analysis of the product showed that much better than 99% of this fraction was $C_7F_{15}COOCH_3$ (83% yield). The major by-product of the reaction was a dimer of perfluorooctanoic acid (490 g).

EXAMPLE 2

A 10 liter stirred tank reactor was loaded with 5.5 liters 1,1,2-trichlorotrifluoroethane. n-Decyl trifluoroacetate (489 g) was diluted with 1,1,2-trichlorotrifluoroethane to give a volume of 1600 ml. The nitrogen flow was set at 2000 cc/min and the fluorine was set at 470 cc/min, the reactor was held at −5° C. After four minutes the decyl trifluoroacetate solution was added at 38 ml per hour. Once all the decyl trifluoroacetate was delivered into the reactor, the fluorine flow was maintained for an additional 15 minutes to ensure perfluorination. After purging fifteen minutes with nitrogen, 200 grams of technical grade methanol was added to the reactor. The products were then distilled to give 903 grams of $C_9F_{19}COOCH_3$ (88.8% Yield) that contained about 0.5% of a material with one or more hydrogens in the fluorinated chain.

EXAMPLE 3

A 10 liter stirred tank reactor was loaded with 5.0 liters 1,1,2-trichlorotrifluoroethane. 260 grams of decanoyl chloride was diluted with 1,1,2-trichlorotrifluoroethane to give 600 ml of solution. The fluorine was set at 600 cc/min with a nitrogen flow of 240 cc/min. The reactor temperature was held at 0° C. After five minutes the decanoyl chloride flow was set at 30 ml/hr. When all of the decanoyl chloride was added (20 hours), the fluorine flow was reduced to 300 cc/min and the nitrogen to 1200 cc/min and held under these conditions for 30 minutes. The fluorine was then turned off and the reactor was purged with nitrogen for 30 minutes after which time 120 grams of methanol was added to the reactor. After distillation 310 grams of $C_9F_{19}COOCH_3$ was recovered (43% yield) with the major by-products being $C_9F_{18}ClCOOCH_3$, $C_9F_{17}Cl_2COOCH_3$, and $C_9F_{20}$.

EXAMPLE 4

A 10 liter stirred tank reactor was loaded with 5.7 liters 1,1,2-trichlorotrifluoroethane. 350 grams of 1,5-pentanediol diacetate was diluted with 1,1,2-trichlorotrifluoroethane to 700 ml. The nitrogen flow was set at 2000 cc/min and the fluorine flow was set at 570 cc/min. After three minutes the flow of 1,5-pentanediol diacetate was set at 30 ml/hr. The reactor temperature was held at −1° C. during the reaction. After all of the pentanediol diacetate had been added (24 hours), the nitrogen flow was set at 1200 cc/min with a fluorine flow of 300 cc/min. Four grams of benzene was placed in 1,1,2-trichlorotrifluoroethane to give 30 ml and this was then pumped into the reactor at a rate of 30 ml/hr for 45 minutes. The benzene flow was then stopped and the fluorine flow was terminated 15 minutes later. After purging with nitrogen, 300 grams of methanol was added to the reactor. After distillation, 457 g (91.5% yield) of the dimethyl ester of 2,2,3,3,4,4-hexafluoropentane-1,5-dioic acid was obtained (b.p. 66°–70° C. at 14 torr). The dimethyl ester can be reduced with lithium aluminum hydride to give a hydroxy-terminated compound with a melt point of 75° C.

$^{19}$F NMR (δ ppm vs $CFCl_3$): −122.6(a) and −126.5(b)

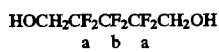

EXAMPLE 5

A 10 liter stirred tank reactor was loaded with 5.0 liter 1,1,2-trichlorotrifluoroethane. 322 grams of hexanediol diacetate was placed in 1,1,2-trichlorotrifluoroethane to give a volume of 640 ml. The nitrogen flow was set at 1.8 liters per minute while the fluorine flow as set at 590 cc/min. After three minutes, the flow of hexanediol diacetate was set at 28 ml/hr. The reactor temperature was held at 0° C. during the reaction. Once all of the hexanediol diacetate had been added (23 hours), the nitrogen flow was reduced to 1200 cc/min and the fluorine flow was reduced to 300 cc/min. Four grams of benzene was diluted to 30 ml with 1,1,2-trichlorotrifluoroethane and added at a rate of 30 ml/hr for 30 minutes. Ten minutes after the benzene flow was stopped, the fluorine was turned off and the reactor purged with nitrogen. 300 grams of technical grade methanol was then added to the reactor to make the dimethyl ester of 2,2,3,3,4,4,5,5-octafluorohexane-1,6-dioic acid. The product was then distilled to give 474 grams of a fraction that had a boiling point of 108°–110° C. at 30 torr (93.5% yield). The product can be reduced with lithium aluminum hydride to give a hydroxy-terminated derivative with a melt point of 65°–66° C.

$^{19}$F NMR (δ ppm vs CFCl$_3$): −122.5(a) and −124.0(b)

HOCH$_2$CF$_2$CF$_2$CF$_2$CF$_2$CH$_2$OH
  a    b    b    a

EXAMPLE 6

5.0 liters 1,1,2-trichlorotrifluoroethane were placed in a 10 liter stirred tank reactor. 291 grams of decanediol diacetate was diluted to 660 ml with 1,1,2-trichlorotrifluoroethane and placed in an erlenmeyer flask. The reactor temperature was held at +10° C. during the reaction while the nitrogen flow was set a 2 liters/minute and the fluorine flow set at 630 cc/min. After 3 minutes the decanediol diacetate solution was added at a rate of 2 ml/hr. Upon completion of the addition (23 hours), the fluorine flow was reduced to 300 cc/min and the nitrogen flow reduced to 1200 cc/min. A solution of 4 grams benzene in 30 ml 1,1,2-trichlorotrifluoroethane was then added at a rate of 30 ml/hr for 30 minutes. The fluorine flow was allowed to continue for an additional 15 minutes then stopped. After purging with nitrogen, 250 grams of methanol was added to the reactor to convert the hydrolytically unstable perfluoroester to the relatively stable methyl esters. 402 grams of material (68.8% yield) was obtained having a boiling point of 102°–113° C. at 0.04 torr. The major impurity was about 150 grams left in the distillation flask that absorbed strongly in the infrared spectrum in the CF and carbonyl regions.

$^{19}$F NMR (δ ppm vs CFCl$_3$): −122.0(b) and −123.7(a)

HOCH$_2$CF$_2$CF$_2$CF$_2$CF$_2$CF$_2$CF$_2$CF$_2$CH$_2$OH
  a    b    b    b    b    b    b    a

EXAMPLE 7

5.0 liters 1,1,2-trichlorotrifluoroethane were placed in a 10 liter stirred tank reactor. 307 grams dimethyl phthalate was diluted to 650 ml and placed in an erlenmeyer flask. The reactor temperature was held at 0° C. during the reaction. The nitrogen flow was set at 1800 cc/min and the fluorine flow set at 460 cc/min. After 3 minutes the dimethyl phthalate solution was added at a rate of 31 ml/hour. Once all the dimethyl phthalate solution was added (21 hours), the nitrogen flow was reduced to 1200 cc/min and the fluorine flow was reduced to 300 cc/min. Four grams of benzene diluted to 30 ml in 1,1,2-trichlorotrifluoroethane was then added to the reactor over a one hour period. The fluorine flow was continued for an additional 15 minutes. After the reactor was purged with nitrogen 280 g methanol was added to the reactor. The products were then distilled at 52 torr to give 171 g of a fraction that boiled below 120° C. and 362 g of a fraction that boiled at 120°–128° C. The first fraction was about 90% pure C$_6$F$_{11}$COOCH$_3$ (31.8% yield) with the diacid as the major impurity. The second fraction was shown by gas chromatography to be about 98% pure C$_6$F$_{10}$(COOCH$_3$)$_2$ (60.2% yield) with an equal mixture there of the cis and trans isomers.

EXAMPLE 8

In order to make perfluoro-2-octanone from an ester of 2-octanol, a trimethyl acetate ester of 2-octanol was used because the resulting perfluoroester is fairly resistant to hydrolysis. 5.0 liters 1,1,2-trichlorotrifluoroethane were placed in a 10 liter stirred tank reactor. 126.5 grams of the trimethyl acetate ester of 2-octanol was diluted to 700 ml in 1,1,2-trichlorotrifluoroethane and placed in an erlenmeyer flask. The reactor temperature was held at −8° C. while the fluorine flow and nitrogen flows were set at 400 and 1500 cc/min, respectively. After three minutes the ester of 2-octanol was added at a rate of 39 ml/hr. Upon completing the addition, the fluorine flow and other conditions were maintained for ten additional minutes after which time the fluorine flow was stopped and the reactor warmed. The product was transferred from the reactor in air with no attempt to do anything extraordinary to prevent hydrolysis. The solvent was removed from the sample by distillation and the bottoms were then transferred to a one liter nickel reactor where 10 cc/min of F$_2$ and 40 cc/min of nitrogen were bubbled through the liquid which was held at 110° C. for four hours to remove any residual hydrogen left in the sample. After purging with nitrogen this sample was then distilled at atmospheric pressure to give 350 grams of a material that boiled at 181°–182° C. (86.8% yield). The fluorinated product (265 g) was hydrolyzed at elevated temperatures with 126 g 1-octanol mixed with 17 g sodium fluoride to give perfluoro-2-octanone which could be easily separated from the 1-octanol by distillation. The product distilled from the flask as formed (b.p. 100°–150° C.). Redistillation of the crude product at 105° C. gave 155 g (96% yield) of perfluoro-2-octanone.

EXAMPLE 9

A 10 liter stirred tank reactor was loaded with 5.4 liters of 1,1,2-trichlorotrifluoroethane and 1415 g of finely ground sodium fluoride powder. The reactor was positioned in a constant temperature bath which maintained a reactor temperature of −7° C. A condenser, which was placed downstream from the reactor, was used to condense and return to the reactor any liquid vapor which may be in the gas exit line. The condenser was maintained at −35° C. A mixture consisting of 328 g of a poly(ethylene glycol) diacetate having an average molecular weight of 600, 320 g of 1,1,2-trichlorotrifluoroethane and 113 g of chloroform (used to solubilize the polyether in the 1,1,2-trichlorotrifluoroethane) was slowly metered into the fluorination reactor over a 26 hour period. Fluorine gas, diluted with nitrogen to give a concentration of 20%, was bubbled through the vigorously stirred fluorination liquid at a rate 10 to 15% higher than that required to theoretically repace all of the hydrogen on the hydrocarbon being pumped into the reactor. Following the reaction, the reactor was purged with several volumes of nitrogen to remove the unreacted fluorine gas. Next, 154 g methanol was pumped into the reactor. The reactor warmed slightly as the perfluorodiester reacted with the methanol to give the hydrolytically more stable dimethyl ester. The product was filtered to remove the sodium fluoride and sodium bifluoride solids. The product (mw 1500), which was obtained in about 80% yield was separated from the 1,1,2-trichlorotrifluoroethane and methanol by distillation.

$^{19}$F NMR of the product in chlorotrifluoromethane gave a small-triplet at −77.7 ppm (vs. CFCl$_3$) and a large singlet at −88.7 ppm corresponding to the terminal and interior difluoromethylene of perfluoropoly(ethylene glycol), respectively.

$$\underset{a\ \ \ \ \ \ \ \ b\ \ \ \ \ \ \ b\ \ \ \ \ \ \ a}{CH_3OCCF_2(CF_2OCF_2)_xCF_2COCH_3}$$
$$\overset{O}{\|} \quad \quad \overset{O}{\|}$$

No definitive peak corresponding to a monofunctional or nonfunctional compound could be seen in the $^{19}$F NMR.

EXAMPLE 10

A 252 g sample of poly(ethylene glycol) having an average molecular weight of 1000 was mixed with 400 g of 1,1,2-trichlorotrifluoroethane and 188 g of trifluoroacetic acid to give a homogeneous solution which was slowly pumped into a 10 liter fluorination reactor containing 5.7 liters of 1,1,2-trichlorotrifluoroethane and 1150 g of sodium fluoride powder. The reactor was maintained at 10° C. as 20% fluorine was delivered at a rate sufficient to react with all of the organic being fed into the reactor. The reaction was complete in approximately 26 hours. Filtration of the product, followed by removal of the fluorination liquid gave 535 g of perfluoropoly(ethylene oxide). Treatment of the fluid for several hours at 250° C. with 30% fluorine converted the reactive terminal groups to perfluoroalkyl groups. The fluid was distilled into fractions having the following physical properties:

| Property | | Fraction 1 | Fraction 2 | Fraction 3 |
|---|---|---|---|---|
| Boiling point range °C. (mm Hg) | | <200(100) | >200(100) <245(10) | >245(10) <288(0.05) |
| % of total | | 13 | 40 | 36 |
| Kinematic Viscosity (cst.) | 20° C. | 3.32 | 13.2 | 33.9 |
| | 40° C. | 2.07 | 7.21 | 16.1 |
| | 60° C. | 1.43 | 4.25 | 9.05 |
| | 80° C. | 1.05 | 2.80 | 5.73 |
| | 95° C. | 0.85 | 2.09 | 4.19 |
| | 149° C. | 0.46 | 1.07 | 1.93 |
| ASTM slope | | 0.934 | 0.725 | 0.681 |
| Density (20° C., g/ml) | | 1.7484 | 1.7650 | 1.7883 |

| Property | | Fraction 4 | Fraction 5 |
|---|---|---|---|
| Boiling point range °C. (mm Hg) | | >288(0.05) <343(0.05) | >343(0.05) |
| % of total | | 7 | 4 |
| Kinematic Viscosity (cst.) | 20° C. | 127.00 | 447.00 |
| | 40° C. | 51.9 | 173.00 |
| | 60° C. | 26.7 | 82.9 |
| | 80° C. | 15.5 | 44.9 |
| | 95° C. | 11.1 | — |
| | 149° C. | 4.27 | 11.4 |
| ASTM slope | | 0.538 | 0.488 |
| Density (20° C., g/ml) | | 1.8133 | 1.8234 |

$^{19}$F NMR of fraction #4 in CFCl$_3$ gave the following results: (δ ppm vs CFCl$_3$) −56.0 (t, 9.6 Hz, a); −89.0 (s,c) and −91.0 (q, 9.6 Hz, b)

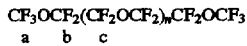

CF$_3$OCF$_2$(CF$_2$OCF$_2$)$_n$CF$_2$OCF$_3$
 a    b    c

Anal. Calcd. for C$_2$F$_4$O: C, 20.69; F, 65.17. Found: C, 20.77; F, 65.29

EXAMPLE 11

In an experiment similar to Example 10, 252 g of a poly(ethylene glycol) having an average molecular weight of 1540 was diluted with 500 ml 1,1,2,-trichlorotrifluoroethane, 87 g trifluoroacetic anhydride and 74 g of trifluoroacetic acid. The homogeneous solution was pumped over a 28 hour period into a 10° C. fluorination reactor containing 5.7 liters of 1,1,2-trichlorotrifluoroethane and 1150 g of sodium fluoride powder. Following filtration and distillation of the product, 398 g of a perfluorinated fluid was recovered (60% yield) along with a small amount of elastomeric solids. The fluid had a composition identical to the fluid described in the previous example and a molecular weight of 2,500 amu.

EXAMPLE 12

A perfluoropolyether elastomer was prepared by dissolving 146 g of an 18,500 a.m.u poly(ethylene glycol) in 354 g of chloroform containing 564 g of 1,1,2-trichlorotrifluoroethane. The viscous solution was slowly pumped into a 10° C. reactor containing 5 liters of 1,1,2-trichlorotrifluoroethane and 800 g of sodium fluoride. Twenty percent fluorine, diluted with nitrogen, was metered into the reactor throughout the reaction which lasted approximately 28 hours. Following the reaction, the product was filtered to give a clear filtrate which contained 14.5 g of a polymeric fluid (3.8%). The insoluble portion of the product consisted of sodium fluoride, sodium bifluoride and perfluoropoly(ethylene oxide) solids (81% yield) having the following structure:

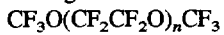

CF$_3$O(CF$_2$CF$_2$O)$_n$CF$_3$

The solids were pressed into thin elastomeric sheets using a laboratory-size mill. The polymer remained elastic over a temperature range of −80° C. to +360° C.

EXAMPLE 13

Five hundred grams of poly(tetramethylene ether) glycol having an average molecular weight of 1000 were treated with a 50% molar excess of acetyl chloride to convert the hydroxyl end groups of the polymer to acetate groups. The acetylated polymer (288 g) was mixed with 500 ml 1,1,2-trichlorotrifluoroethane and was slowly pumped into a 10 liter reactor containing 5 liters of 1,1,2-trichlorotrifluoroethane and 1400 g of sodium fluoride powder. The reactor temperature was maintained at 5° C. while 20% fluorine was metered into the reactor at a rate sufficient to react with the organic being delivered. Following the reaction, the product was filtered to remove the sodium fluoride and the filtrate was concentrated to give 700 g of a fluorinated oil (81% yield) which was treated for 12 hours at 270° C. with 30% fluorine to remove any remaining hydrogens and to convert the terminal esters to nonreactive perfluoroalkyl groups. Approximately 40% of the oil distilled between 200° and 300° C. at 0.05 mm Hg. The average molecular weight by $^{19}$F NMR end group analysis was 3054. The fluid had a pour point of −50° C.

| Viscosity of Perfluoropoly(tetramethylene ether) glycol | | |
|---|---|---|
| Temperature °C. | Viscosity (cst.) | Slope ASTM #D341 |
| 20 | 164.9 | |
| 80 | 14.61 | −0.654 |
| 150 | 3.29 | |

| $^{19}$F NMR data for Perfluoropoly(tetramethylene ether) glycol | | | |
|---|---|---|---|
| Structure | δ (Multiplicity) ppm vs CFCl$_3$ | J(F—F) Hz | Rel. Inten. % |
| C$\underline{F}_3$O | −55.7 (t) | 18.3 | 0.2 |
| C$\underline{F}_3$CF$_2$CF$_2$O | −81.9 (t) | 7.3 | 4.9 |
| OC$\underline{F}_2$CF$_2$CF$_2$C$\underline{F}_2$O | −83.3 (s) | | 42.6 |
| CF$_3$C$\underline{F}_2$CF$_2$O | −84.3 (m) | | 3.3 |
| C$\underline{F}_3$CF$_2$O | −87.3 (s) | | 0.9 |
| CF$_3$C$\underline{F}_2$O | −88.5 (p) | | 0.5 |
| OCF$_2$C$\underline{F}_2$C$\underline{F}_2$CF$_2$O | −125.7 (s) | | 42.6 |
| CF$_3$C$\underline{F}_2$CF$_2$O | −130.0 (s) | | 3.3 |

Anal. Calcd. for CF$_3$CF$_2$CF$_2$O(CF$_2$CF$_2$CF$_2$CF$_2$O)$_{12.5}$CF$_2$CF$_2$CF$_3$: C, 22.00; F, 70.92. Found: C, 21.87; F, 70.02

EXAMPLE 14

Using the procedures outlined in Example 9, a solution consisting of 280 g of poly(tetramethylene ether) glycol (terminal groups treated with acetyl chloride to give a diester) having an average molecular weight of 2000 and 550 ml of 1,1,2-trichlorotrifluoroethane was slowly metered, over a 32 hour period, into a 5° C. fluorination reactor containing 5 liters of 1,1,2-trichlorotrifluoroethane and 1400 g of sodium fluoride powder. Upon completing the reaction, the reactor was purged with several volumes of nitrogen to remove the unreacted fluorine gas. Methanol (150 g) was added to the reactor. The reactor contents were filtered to give a clear filtrate which upon removal of the 1,1,2-trichlorotrifluoroethane and unreacted methanol via a distillation gave a nearly quantitative yield of perfluoropoly (tetramethylene ether) dimethyl ester (mw 4250).

EXAMPLE 15

Into a 500 cc stainless steel pressure vessel were placed 250 g 1,2-epoxybutane and 1 g ferric chloride catalyst. The reactor was rocked in an 80° C. oven for approximately 96 hours during which time the epoxide polymerized to give a high molecular weight semisolid. The polymer was dissolved in 1 liter of 1,1,2-trichlorotrifluoroethane and pumped into a fluorination reactor using the procedures outlined in Example 9. The reactor, which contained 5 liters of 1,1,2-trichlorotrifluoroethane and 1250 g sodium fluoride powder, was held at 0° C. with a constant temperature bath. Following the 22 hour reaction, 750 g of fluid was recovered which was further fluorinated at 300° C. with 30% fluorine for an additional 24 hours to give 660 g of fluid (88% yield). Approximately 220 g of fluid distilled between 200 and 3000° C. at reduced pressure (0.05 mm Hg) with approximately equal amounts boiling below and above that range. The average molecular weight of the mid-fraction was 1850 (by $^{19}$F NMR end group analysis). The fluid had a pour point of −9° C.

| Viscosity Of Perfluoropoly(1,2-epoxybutane) bp >200° C. and <300° C. @ 0.05 mm Hg | | |
|---|---|---|
| Temp (°C.) | Viscosity (cst.) | Slope ASTM #D341 |
| 20 | 5688 | |
| 80 | 72.9 | −0.725 |
| 150 | 6.52 | |

| $^{19}$F NMR of Perfluoropoly(1,2-epoxybutane) | | |
|---|---|---|
| Structure | δ(Multiplicity) ppm vs CFCl$_3$ | Rel. Inten. % |
| CF$_2$CF(C$_2$F$_5$)O | −77.3, −80.01, 82.2 | 23.3 |
| CF$_2$CF(CF$_2$CF$_3$)O | −81.0 (s) | 35.3 |
| CF$_3$CF$_2$CF$_2$O | −82.0 (m) | 4.2 |
| CF$_3$CF$_2$CF$_2$O | −84.7 (m) | 2.8 |
| CF$_2$CF(CF$_2$CF$_3$)O | −120 to 127 | 23.3 |
| CF$_3$CF$_2$CF$_2$O | −130.3 | 2.8 |
| CF$_2$CF(C$_2$F$_5$)O | −141.2 (m) | 7.8 |

EXAMPLE 16

A potentially useful nonflammable hydraulic fluid was prepared by placing in a 3 liter, 3 neck flask equipped with a mechanical stirrer, 80 g 2-chloroethanol (1.0 mol) and 1 ml boron trifluoride-etherate. To this solution, 462 g epichlorohydrin (5.0 mol) was added over a one hour period while the reaction temperature was maintained below 50° C. throughout the addition. The mixture was stirred for an additional 12 hours at ambient temperature resulting in the formation of a very viscous fluid. The product (403 g) was dissolved in 164 g chloroform containing 405 g 1,1,2-trichlorotrifluoroethane. This solution was metered into an 18° C. reactor which contained 5 liters of 1,1,2-trichlorotrifluoroethane. Fluorine gas (20%) was introduced at a rate which was approximately 5% greater than the theoretical amount required to react with all of the hydrogens on the material entering the reactor. Upon completion of the reaction which lasted approximately 20 hours, the reactor was purged with nitrogen to remove the unreacted fluorine gas.

Distillation of the product to remove the fluorination liquid gave 620 g of a perfluorinated fluid having substantially the following structure:

ClCF$_2$CF$_2$(CF$_2$CF(CF$_2$Cl)O)$_n$CF$_2$CF$_2$Cl

M.W. 868; Density (37.8° C.): 1.7973 g/ml Bulk modulus (37.8° C. and 3,000 PSIG): 129, 700 PSIG Elemental Analysis: Calculated for an average structure $C_{2.11}F_{4.42}Cl_{0.8}O(C_3F_5ClO)_{3.05}C_{2.11}F_{4.42}Cl_{0.8}$ C, 18.92; F, 53.98; Cl, 1944 Found: C, 18.86; F, 51.15; Cl, 18.26% A further treatment of the above product with 30% fluorine at 225° C. converted the carbonyl to a difluoromethylene group (618 g). Following treatment of the product at elevated temperatures with fluorine the product was distilled. The portion boiling between 50° C. and 150° C. at 2 mm Hg was collected (80% of the sample) and was shown to be a very promising hydraulic fluid candidate. The bulk modulus of the material was measured using an isothermal secant method. The following results were obtained.

| Perfluoropolyepichlorohydrin Type I Bulk Modulus $M_a$ @ PSI | | | | |
|---|---|---|---|---|
| °F. @ PSI | 1000 | 2000 | 3000 | 4000 |
| 100° F. | 129,500 | 136,700 | 138,600 | 145,100 |
| 150° F. | 180,700 | 104,200 | 109,700 | 115,400 |

| Viscosity of Perfluoropolyepichlorohydrin Type I Hydraulic Fluid (monochloro end group) | |
|---|---|
| Temp °F. | Viscosity (cst.) |
| −65 | 1198 |
| 100 | 3.5 |
| 176 | 1.42 |

EXAMPLE 17

A high molecular weight perfluoropolyepichlorohydrin fluid, having properties similar to those required for a vacuum pump fluid, was prepared by reacting 50 g 2-chloroethanol (0.63 mol) with 462 g epichlorohydrin (5.0 mol) using a catalytic amount of SnCl$_4$. The product (402 g), diluted with 275 g chloroform and 175 g 1,1,2-trichlorotrifluoroethane, was metered into a fluorination reactor over a 20 hour period. The reactor, a 10 liter stirred tank, contained 5.7 liters 1,1,2-trichlorotrifluoroethane. During the course of the reaction the temperature was maintained near 20° C. while 20% fluorine was delivered to the reactor at a rate sufficient to react with all of the hydrogens on the product being pumped in. The fluorinated product (573 g, 89.8% yield) was separated from the solvent via an atmospheric distillation. The product was treated at 200° C. for 12 hours to remove any residual hydrogen and to convert any carbonyl groups present to difluoromethylenes. The portion of the product, approximately 25%, having a boiling point between 200° and 300° C. at 0.05 mm Hg was collected. The average molecular weight by $^{19}$F NMR end group analysis was approximately 3000. The fluid had a pour point of −22° C.

| Viscosity Of Perfluoropolyepichlorohydrin Vacuum Pump Fluid | | |
|---|---|---|
| Temp. (°C.) | Viscosity (cst.) | Slope ASTM #D341 |
| 20 | 953.7 | |
| 80 | 26.54 | 0.763 |
| 150 | 4.11 | |

$^{19}$F NMR of fraction boiling between 200° and 300° C. at 0.05 mm Hg (δ ppm vs CFCl$_3$); −53.3(f), −67.2(e), −68.6(i), −74.2(a), −77.0 & −81.0(c), −79.0(g), −87.3(b), −123.7(h), and −139.3(d).

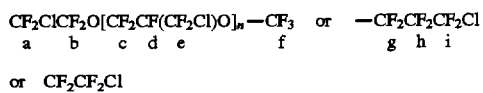

EXAMPLE 18

Into a 10 liter, 3 neck flask equipped with a mechanical stirrer were charged 860 g 1,3-dichloro-2-propanol (617 mol) and 4 ml boron trifluoride-etherate. To this solution was added 1.8 Kg epichlorohydrin (20 mol) over a 2 hour period as the temperature was maintained below 50° C. throughout the addition with a water bath. The mixture was stirred for an additional 12 hours at ambient temperature resulting in a very viscous oil.

A portion of the above epichlorohydrin telomer (1,660 g) was dissolved in 164 g chloroform containing 405 g 1,1,2-trichlorotrifluoroethane. The solution was metered into a 10 liter stirred fluorination reactor containing 5.0 liters of 1,1,2-trichlorotrifluoroethane. The reactor was held at 20° C. throughout the addition as fluorine gas (20%), diluted with nitrogen, was delivered at a rate slightly above that required to theoretically react with all of the organic feed. The reaction was complete in 36 hours. The crude product was recovered from the solvent by an atmospheric distillation. Treatment of the product with 30% fluorine at 200° C. for 12 hours resulted in 4100 g of an inert fluid of which approximately 80% boiled between 50 and 150° C. at 2 mm Hg.

The fluid was shown by $^{19}$F NMR end group analysis to have an average molecular weight of 850.

Density (37.8° C.): 1.7966 g/ml

Bulk modulus (37.8° C. and 3,000 PSIG): 135,400 PSIG

Elemental analysis calculated for an average structure of: $C_{2.31}F_{4.46}Cl_{1.15}O(C_3F_5ClO)_{2.89}C_{2.31}F_{4.46}Cl_{1.15}$ C, 18.77; F, 52.26; Cl, 21.65 Found: C, 18.85; F, 53.13; Cl, 21.51%

| Viscosity of Perfluoropolyepichlorohydrin Type II Hydraulic Fluid (Dichloro end group) | |
|---|---|
| Temp (°F.) | Viscosity (cst.) |
| −65 | 1130 |
| 100 | 3.35 |

$^{19}$F NMR (δ ppm vs CFCl$_3$) −53.3(f), −65.6(a), −67.2(e), −68.6(k), −74.3(h), −77.0(c), −79.0(i), −87.3(g), −123.7(j), −135.2(b) and −139.3(d).

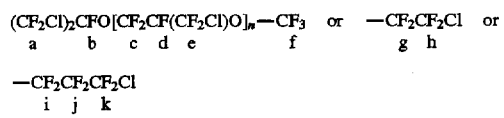

EXAMPLE 19

Trichloropentaerythritol was prepared by bubbling hydrogen chloride gas into a mixture of 600 g acetic acid and 100 g of rarer at 0° C. until 176 g had been absorbed (4.9 mol). This mixture was charged into an autoclave along with 200 g pentaerythritol (1.5 mol). The autoclave was sealed and heated to 160° C. for 8 hours. Upon completion of the reaction, the autoclave was cooled to room temperature and the reaction mixture was diluted with water. Trichloropentaerythritol acetate was isolated by extraction with methylene chloride. The solvent was removed and the residual oil was refluxed overnight with 500 ml of methanol and 50 ml of concentrated hydrochloric acid. Trichloropentaerythritol crystallized from the solution as the methanol and methyl acetate was slowly removed by distillation. The crude product (275 g) has a melting point of 60° C.

A 3 liter flask was charged with 267 g of trichloropentaerythritol and 1 ml of boron trifluoride-etherate. To this was added 347 g of epichlorohydrin (3.75 mol) dropwise over a one hour period while the reaction temperature was maintained below 50° C. throughout the addition. The mixture was stirred for an additional 12 hours at ambient temperature resulting in a viscous oil.

The product (612 g), diluted with 210 g of chloroform and 217 g of 1,1,2-trichlorotrifluoroethane, was fluorinated in the usual manner in a 20° C. reactor containing 3.7 liters of 1,1,2-trichlorotrifluoroethane. The reaction was complete in approximately 30 hours. The fluid (1,460 g) was stabilized by treatment with 30% fluorine for 12 hours at 210° C. The fluid was distilled and the portion boiling between 170° C. and 230° C. at 50 mm Hg had a viscosity suitable for hydraulic fluid applications. Average molecular weight of the product was 855.

| Viscosity of Perfluoroepichlorohydrin Type III Hydraulic Fluid (Trichloro end groups) | |
|---|---|
| Temp (°F.) | Viscosity (cst.) |
| −65 | 1150 |
| 104 | 3.06 |
| 176 | 1.46 |

$^{19}$F NMR (δ ppm vs CFCl$_3$) −48.7(a), −53.3(f), −67.2(e), −68.5(k), −74.3(h), −77.0(c), −78.8(1), −80.6(b), −87.3(g), −123.8(j) and −140(d).

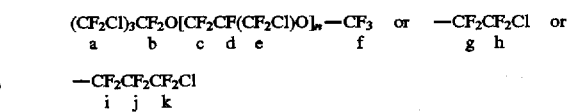

EXAMPLE 20

Butoxyethoxyethanol (300 g. 1.85 mol) was treated with 200 g acetyl chloride (2.54 mol) to give an ester which was separated from the produce mixture by distillation. A portion of the product (250 g) was diluted to a volume of 610 ml with 1,1,2-trichlorotrifluoroethane, then pumped into a −10° C. reactor over a 23 hour period. Fluorine gas, diluted with nitrogen, was delivered to the reactor which contained 5 liters of 1,1,2-trichlorotrifluoroethane and 1200 g sodium fluoride powder.

Upon completion of the reaction, 160 g methanol was pumped into the reactor to give the methyl ester which is considerably more hydrolytically stable than the perfluoro ester made in the reaction. The product (M.W. 460) was obtained in 96% yield.

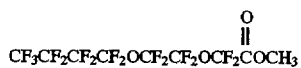

EXAMPLE 21

A diacetate ester of tetraethylene glycol was prepared by slowly adding 600 g acetyl chloride to 500 g tetraethylene glycol in a stirred 2-liter flask. Upon addition of the acetyl chloride, the reaction mixture was heated to 50° C. and held at that temperature for 24 hours. Dry nitrogen was bubbled through the flask for 24 hours to remove the hydrogen chloride, then the product was distilled to give a quantitative yield of the desired product.

The product from the above reaction (247.7 g) was fluorinated in a reactor containing 5 liters 1,1,2-trichlorotrifluoroethane and 120 g sodium fluoride. The reactor was held at −10° C. for approximately 20 hours as the organic was slowly pumped into the reactor. Upon completion of the addition, the unreacted fluorine was swept from the reactor with nitrogen gas and 200 g of methanol was added to give the following product in 93% yield (M.W. 466).

$^{19}$F NMR (δ ppm vs CFCl$_3$): −77.6(a) and −88.4(b).

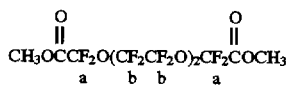

The above product was reduced with lithium aluminum hydride in tetrahydrofuran to give the expected methylol derivative in approximately 90% yield.

EXAMPLE 22

A diacetate ester of triethylene glycol was prepared by slowly adding 400 g acetyl chloride (5.1 mol) to 300 g triethylene glycol (2.0 mol) in a stirred 1 liter flask. The reaction mixture was kept below 50° C. throughout the addition. The product was recovered by first bubbling dry nitrogen through the solution to remove most of the hydrogen chloride followed by a distillation.

The product from the above reaction (250 g) was diluted to 600 ml with 1,1,2-trichlorotrifluoroethane then pumped into a −20° C. reactor containing 5 liters of 1,1,2-trichlorotrifluoroethane and 1200 g sodium fluoride powder. Fluorine, diluted with nitrogen, was bubbled through the liquid fluorination medium throughout the addition which required approximately 18 hours. After purging the reactor for approximately 30 minutes, 240 g methanol was added and the reactor was warmed to room temperature. Distillation of the reactor contents gave 355 grams (95% yield) of a product with the following composition.

$^{19}$F NMR (δ ppm vs CFCl$_3$): −77.6(a) and −88.3(b)

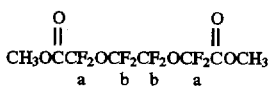

The dimethyl ester was reduced with lithium aluminum anhydride to give the methylol derivative.

$^{19}$F NMR (δ ppm vs CFCl$_3$): −80.3(a) and −89.0(b)

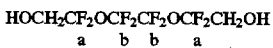

EXAMPLE 23

A 200 g sample of polypropylene glycol having an average molecular weight of 425 was diluted to 350 ml with 1,1,2-trichlorotrifluoroethane and slowly pumped into a 20° C. fluorination reactor over a 22 hour period. The reactor contained 4 liters of 1,1,2-trichlorotrifluoroethane as the fluorination liquid. In a separate vessel, 1000 g sodium fluoride pellets were placed. A teflon-diaphragm air pump was used to circulate the gases present in the reactor through the sodium fluoride bed and back into the fluorination reactor. Gas velocities in the recirculating loop of approximately 10 to 20 liters per minute were sufficient to sweep out most of the hydrogen fluoride formed in the reaction so that reasonable fluorination yields could be achieved. Following the reaction, 307 g of product (M.W. 1200) was isolated by distillation (53.7%)

EXAMPLE 24

In an experiment similar to the one previously described, 202 g polypropylene glycol (425 MW) was fluorinated in a reactor containing 3.7 liters of 1,1,2-trichlorotrifluoroethane. Once again, 1000 g sodium fluoride pellets were placed in a container which was connected to the fluorination reactor by a circulating gas loop. The reaction temperature was increased to 30° C. to see if the hydrogen fluoride could be removed more efficiently. The product (356 g) was isolated in 62.2% yield.

Unlike the isotactic perfluoropoly(propylene oxide) which can be made by polymerizing hexafluoropropylene oxide, the perfluorinated fluids described in this example and the previous one were atactic polymers of hexafluoropropylene oxide. The hexafluoropropylene oxide units were attached in a head to tail, head to head and tail to tail fashion. Because of the random structure of these fluids, slightly improved low temperature properties were typically obtained.

EXAMPLE 25

To a stirred solution consisting of 194 g tetraethylene glycol (1.0 mol) and 4.0 g of 50% sodium hydroxide was added 111 g acrylonitrile (2.1 mol). The reaction mixture was stirred for three hours at room temperature. 500 ml ethanol was added to the mixture followed by the slow addition of 214 ml of concentrated sulfuric acid (4.0 mol). Upon completion of the addition, the mixture was refluxed for seven hours, cooled, then filtered to remove the precipitated solids (NH$_4$HSO$_4$). The solids were washed with ethanol and the organic phase was combined with the ethanol rinse solution to give a mixture which upon distillation yielded a product with the following structure (90% yield).

Fluorination of 305 grams of the polyether in a 10° C. reactor containing 5 liters of 1,1,2-trichlorotrifluoroethane and 1200 g sodium fluoride, followed by treatment with methanol gave 568 g of fluid (M.W. 798) having the following structure (92% yield).

EXAMPLE 26

In an experiment similar to the previous one, 194 g tetraethylene glycol (1.0 mol) was reacted with 140 g methacrylonitrile (2.1 mol) in the presence of 4.0 g 50% sodium hydroxide. Treatment of the resulting dinitrile with ethanol and concentrated sulfuric acid yielded the diethyl ester.

Fluorination of the diester (300 g) using a fluorination procedure similar to that described in the previous example gave 630 g of the product shown below (91% yield).

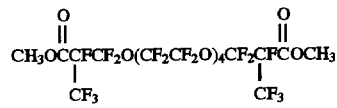

EXAMPLE 27

Using the procedure outlined in Example 25, dipropylene glycol methyl ether was treated with acetonitrile to give a material which upon treatment with ethanol in the presence of sulfuric acid gave of material having the following structure:

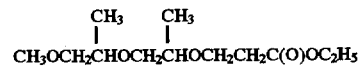

Fluorination of 213 of the material in a −10° C. reactor containing 5.3 liters of 1,1,2-trichlorotrifluoroethane and 1050 g of sodium fluoride powder gave a perfluorinated ester which upon treatment with methanol gave 258 of a functional fluid corresponding to the following structure.

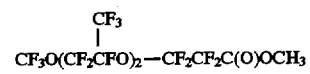

bp 75° C./15 mm Hg

EXAMPLE 28

Cyclohexene oxide (250 g) was polymerized in 1 liter of n-hexane at −0° C. using a catalytic amount of triethylaluminum. The reaction was complete in approximately 1 hour. The polymer was first washed with concentrated HCl, then water followed by several rinses with methanol.

Fluorination of the polymer (205 g) using the fluorination techniques outlined in previous examples gave 413 g of a perfluorinated fluid (71% yield).

EXAMPLE 29

200 g polyoxetane was diluted to a volume of 500 ml and was slowly pumped into a 20° C. fluorination reactor containing 5 liters 1,1,2-trichlorotrifluoroethane and 1000 g sodium fluoride powder. The polymer was prepared via a ring opening polymerization of oxetane or by dehydration of 1,3-propanediol. The fluorinated product, 335 g, was recovered by first removing the sodium fluoride by filtration followed by distillation to remove the fluorination solvent.

$^{19}$F NMR of a sample having a boiling point of 200°–300° C./0.05 mm Hg: (δ ppm vs CFCl$_3$) −83.3 (s,a), −129.2 (s,b)

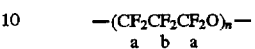

EXAMPLE 30

Into a 1 liter stirred flask equipped with a water separator were placed 500 g diethylene glycol (4.7 mol), 90 g diethylene glycol methyl ether (10.75 mol), 225 g paraformaldehyde (7.5 mol), 150 ml toluene and 5 g ion exchange resin (H$^+$ form). The mixture was refluxed for several hours to remove the water formed during the reaction. The solution was first filtered to remove the ion exchange resin, then distilled to 150° C. at 0.05 mm/Hg to remove the toluene and other lights. A nearly quantitative yield of polymer having an average molecular weight of 1500 was obtained.

320 g of polymer, mixed with 170 g chloroform and 300 g 1,1,2-trichlorotrifluoroethane was slowly pumped over a 23 hour period into a 15 liter stirred fluorination reactor containing 6 liters of 1,1,2-trichlorotrifluoroethane and 1300 g of sodium fluoride powder. 20% fluorine was bubbled through the liquid fluorination medium at a rate 15% higher than that required to theoretically replace all of the hydrogen on the hydrocarbon being pumped into the reactor. The reactor temperature was maintained between 0° and +10° C. throughout the reaction. Following the reaction, the reactor contents were filtered and the liquid fluorination medium (1,1,2-trichlorotrifluoroethane) was removed from the filtrate via an atmospheric distillation to 120° C. to give 535 g of crude fluid (66%). Fluorination of the fluid at 260° C. gave a clear, colorless fluid which was shown by elemental analysis and $^{19}$F NMR to have the following structure:

EXAMPLE 31

400 g butoxyethoxyethanol (2.5 mol), 48 g paraformaldehyde (1.6 mol), 300 ml benzene and 5 g ion exchange resin (acid form) were placed in a 1 liter stirred flask. A water separator attached to a reflux condenser was used to collect the water produced as the alcohol and aldehyde reacted. After approximately 6 hours, the reaction was complete and the solution was filtered to remove the resin. Vacuum distillation of the solution to 120° C. gave 414 g of a product (99% yield) which was essentially free of benzene and unreacted starting materials.

The hydrocarbon product was fluorinated in a 22 liter stirred tank reactor which contained 6 liters of 1,1,2-trichlorotrifluoroethane and 1300 g sodium fluoride powder. A gas dispersion tube in the bottom of the reactor provided an inlet for the fluorine and nitrogen gasses. 275 grams of the hydrocarbon reactant was diluted with 1,1,2-trichlorotrifluoroethane, in a separate vessel, to give a total volume of 700 ml. This solution was metered into the fluorination reactor over a 20 hour period. The reactor temperature was maintained at 0° C. with external cooling throughout the reaction while the fluorine flow was set at a level 10% higher than that required to theoretically replace all of the hydrogens on the material entering the reactor.

Upon completion of the reaction, the fluorine was turned off, the reactor was removed from the low temperature bath and purged for 30 min with nitrogen (2 liters/min) to remove the unreacted fluorine.

Filtration of the reaction product followed by distillation to remove the 1,1,2-trichlorotrifluoroethane gave 642 g of a highly fluorinated fluid (80% yield). Treatment of the fluid at 260° C. with 30% fluorine for several hours gave a perfluorinated fluid having essentially the following structure:

$CF_3CF_2CF_2CF_2OCF_2CF_2OCF_2CF_2OCF_2CF_2OCF_2CF_2OCF_2CF_2CF_3$

The elemental analysis was consistent with the formula: $C_{17}F_{36}O_6$.

b.p. 226.5° C.

$^{19}F$ NMR (δ ppm vs $CFCl_3$): −89.0. −90.7: $CF_2CF_2O$; −51.8: $CF_2O$; −81.8. −83.7. −126.7: $CF_3CF_2CF_2CF_2O$.

EXAMPLE 32

A mixture of 400 g triethylene glycol monoethyl ether (2.2 mol), 48 g paraformaldehyde (1.6 mol), 150 ml toluene and 10 g of an acid ion exchange resin was refluxed for 6 hours in a 1 liter flask equipped with a water separator and reflux condenser. Filtration of the product followed by distillation gave a quantitative yield of the desired product.

Fluorination of 201 g of the material in a stirred liquid fluorination reactor containing 6 liters of 1,1,2-trichlorotrifluoroethane and 1055 g sodium fluoride gave 401 g fluid in an 18 hour reaction at 0° C. Distillation of the crude product mixture gave 355 g of the perfluorinated fluid:

$CF_3CF_2OCF_2CF_2OCF_2CF_2OCF_2CF_2OCF_2OCF_2CF_2$
$OCF_2CF_2OCF_2CF_2OCF_2CF_3$ $C_{17}O_8F_{36}$
b.p. 217° C.

$^{19}F$ NMR (δ ppm vs $CFCl_3$): −51.7: $CF_2O$; −87.3, −90.7: $CF_3CF_2$; −88.7 $CF_2CF_2O$.

EXAMPLE 33

Into a 1 liter flask were placed 600 g triethylene glycol butyl ether (2.91 mol), 74 g paraformaldehyde (2.46 mol), 150 ml benzene and 10 g of an acidic ion exchange resin. The mixture was refluxed for 5 hours as water was removed as the water/benzene azeotrope. Filtration of the product and removal of the benzene by distillation gave a 90% yield of the polyether. 259 grams of the product was diluted with 400 ml 1,1,2-trichlorotrifluoroethane and was slowly metered into a 10° C. reactor containing 5.7 liters of 1,1,2-trichlorotrifluoroethane and 1200 g sodium fluoride powder. A fluorocarbon fluid (660 g, 88.7% yield) was obtained following filtration and removal of the 1,1,2-trichlorotrifluoroethane. Fluorination of the fluid at 220° C. with 30% fluorine for 12 hours followed by distillation gave the following fluid in 60% yield:

$CF_3CF_2CF_2CF_2OCF_2CF_2OCF_2CF_2OCF_2CF_2OCF_2$
$CF_2OCF_2CF_2OCF_2CF_2OCF_2CF_2CF_3$
b.p. 262° C.

$^{19}F$ NMR (δ ppm vs $CFCl_3$): −88.7, −90.5; $CF_2CF_2O$; −51.7: $CF_2O$; −81.6, −83.4, −126.5: $CF_3CF_2CF_2CF_2O$.

EXAMPLE 34

Into a stirred 1 liter flask equipped with a water separator were charged 350 g tetraethylene glycol butyl ether (1.40 mol), 35 g paraformaldehyde (1.18 mol), 200 ml benzene and 10 g ion exchange resin. The mixture was refluxed until the water production ceased. Filtration of the product followed by removal of the lights via a vacuum distillation to 140° C. gave 343 g of a light yellow fluid.

A 306 g sample of the fluid was diluted with 450 ml of 1,1,2-trichlorotrifluoroethane and slowly pumped into a −6° C. reactor over a 23 hour period. The reactor contained 1450 g of sodium fluoride powder to react with the hydrogen fluoride formed during the reaction along with 6 liters of 1,1,2-trichlorotrifluoroethane. Filtration of the product followed by distillation gave 736 g of fluid.

Treatment of the fluid at 250° C. with 30% fluorine gave a clear, odorless fluid which upon distillation gave a 52% yield of a material having the following structure:

$CF_3CF_2CF_2CF_2OCF_2CF_2OCF_2CF_2OCF_2CF_2OCF_2CF_2$
$OCF_2OCF_2CF_2OCF_2CF_2OCF_2OCF_2CF_2OCF_2CF_2CF_2$
$CF_3$ b.p. 296.7° C.

$^{19}F$ NMR (δ ppm vs $CFCl_3$): −51.8: $CF_2O$; −88.8, −90.6: $CF_2CF_2O$; −81.7, −83.6, −126.7: $CF_3CF_2CF_2CF_2O$.

EXAMPLE 35

In a similar experiment, 400 g tetraethylene glycol (2.06 mol), 109 g paraformaldehyde (3.62 mol), 17 g triethylene glycol methyl ether (0.103 mol), 150 ml benzene and 5 g ion exchange resin were allowed to react in a 1 liter flask containing a water separator. After 6 hours, the contents of the flask were filtered and the lights were removed via a vacuum filtration. A 265 g sample of the polymer was mixed with 160 g chloroform and 285 g 1,1,2-trichlorotrifluoroethane. The polymeric solution was metered, over a 22 hour period, into a stirred 10 liter fluorination reactor which contained 1150 g sodium fluoride powder and 4.5 liters of 1,1,2-trichlorotrifluoroethane. The reactor was maintained at 7° C. while 20% fluorine (diluted with nitrogen) was metered into the reactor at a rate sufficient to react with all of the organic entering the reactor. Upon completion of the reaction, the solution was filtered and the liquid fluorination medium was removed via a distillation yielding 422 g (62% yield) of a clear, stable fluid. The product was fractionated into three samples, one which boiled below 200° C. at 0.05 mm Hg (40%), a second which boiled between 200° and 300° C. at 0.05 mm (35%) and a third having a boiling point above 300° C. at 0.05 mm Hg (25%). The intermediate fraction had a viscosity of 33.1 cst. at 20°, 6.3 cst. at 80° and 2.13 cst. at 150° C. and an average molecular weight of 2560 by $^{19}F$ NMR. The pour point was −79° C. The analysis was consistent with the formula:

$(CF_2CF_2OCF_2CF_2OCF_2CF_2OCF_2CF_2OCF_2O)_n$ $^{19}F$ NMR (δ ppm vs $CFCl_3$) −51.8: $CF_2O$; −56.0: $CF_3O$; −88.8, −90.6: $CF_2CF_2O$. Anal. Calcd. for $C_9F_{18}O_5$: 20.4, C; 64.5, F. Found. 21.0, C; 65.1, F.

EXAMPLE 36

Dipropylene glycol methyl ether (300 g, 2.04 mol), 60.8 g paraformaldehyde (2.03 mol), 100 ml toluene and 5 g of an acid catalyst were mixed in a stirred 1 liter flask. After refluxing for 12 hours, the solution was filtered and distilled to give 203 g of a fluid which boiled at 140° C. at 0.05 mm Hg. The fluid (200 g) was mixed with 300 ml 1,1,2-trichlorotrifluoroethane and 950 g sodium fluoride powder. The reaction was complete in 18 hours after which time the solution was filtered and distilled to give 405 g of a clear liquid having the following structure (71% yield):

$CF_3OC_3F_6OC_3F_6OCF_2OC_3F_6OC_3F_6OCF_3$

The fluid contains $CF(CF_3)CF_2OCF(CF_3)CF_2O$, $CF(CF_3)CF_2OCF_2CF(CF_3)O$ and $CF_2CF(CF_3)OCF(CF_3)CF_2O$ linkages. The structure was confirmed by $^{19}F$ NMR and elemental analysis:

$^{19}$F NMR (δ ppm vs CFCl$_3$): −47.6: CF$_3$O; −54.0: CF$_2$O; −80.0: CF(CF$_3$)CF$_2$O; −82 to −87: CF(CF$_3$)CF$_2$O; −140 to 150; CF(CF$_3$)CF$_2$O.

EXAMPLE 37

A mixture of 300 g tripropylene glycol methyl ether (6.46 mol), 33.7 g paraformaldehyde (1.12 mol), 150 ml benzene and 3 g ion exchange resin was refluxed for 6 hours in a 1 liter flask equipped with a water separator and reflux condenser. Filtration of the product followed by vacuum distillation of the lights gave 166 g of a product with a boiling point above 150° C. at 0.05 mm Hg.

Fluorination of 145 g of the material, dissolved in 450 ml 1,1,2-trichlorotrifluoroethane, in a stirred fluorination reactor containing 6 liters of 1,1,2-trichlorotrifluoroethane and 700 g of sodium fluoride gave 244 g of a fluorocarbon product in a 20 hour reaction at −3° C. Distillation of the product gave 180 g of the perfluorinated fluid:

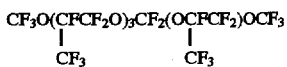

where the hexafluoropropylene oxide units are attached randomly in a head to head, head to tail and tail to tail fashion.

$^{19}$F NMR (δ ppm vs CFCl$_3$): −47.3, −56.0: CF$_3$O; 54.0: CF$_2$O; −80.0 CF(CF$_3$)CF$_2$O; −83.0, −85.3: CF(CF$_3$)CF$_2$O; −145.3, −146.3: O:CF(CF$_3$)CF$_2$O.

b.p. 260.0° C.

EXAMPLE 38

A mixture of 400 g dipropylene glycol (3.0 mol), 358 g paraformaldehyde (12 mol), 150 ml toluene and 10 g ion exchange resin was refluxed for 5 hours in a stirred 1 liter flask equipped with a water separator. The ion exchange resin was removed prior to distillation of the mixture to 150° C. under a full vacuum to remove any low molecular weight polymer. Approximately 200 g of polymer remained in the flask which was shown by gel permeation chromatography to have an average molecular weight of approximately 3000.

The polymer, 280 g, was mixed with 340 ml 1,1,2-trichlorotrifluoroethane and was slowly pumped into a 15 liter stirred reactor over a 24 hour period. The reactor, which contained 5.5 liters of 1,1,2-trichlorotrifluoroethane and 1220 g sodium fluoride powder, was maintained at 10° C. throughout the reaction while 20% fluorine was bubbled through the liquid fluorination medium at a rate just exceeding that required to react with all of the starting material being pumped into the reactor. The reactor contents were filtered and distilled to give 587 g of fluid which was further treated with 50% fluorine at 270° C. to give a fluid which was essentially free of hydrogen. The purified product was fractionated into three samples. The first fraction boiled below 200° C. at 0.05 mm Hg, the second distilled over between 200° and 300° C. at 0.05 mm and the distillation bottoms had a boiling point above 300° C. at 0.05 mm Hg. The second fraction comprised approximately 20% of the total fluid with the majority of the sample having a boiling point below 200° C. at 0.05 mm. The second fraction had an average molecular weight of 2500 by $^{19}$F NMR.

The viscosity of the second fraction at 20° C. was 72.2 cst. (ASTM slope of 0.644). The pour point was −62° C.

$^{19}$F NMR (δ ppm vs CFCl$_3$): −47.3, −49.3, −51.4: CF$_2$O; −54.0, −55.8: CF$_3$O; −79.7: OCF(CF$_3$)CF$_2$O; −81.8, −82.8, −84.7: OCF(CF$_3$)CF$_2$O; −87.3: CF$_3$CF$_2$O; −130.0: CF$_3$CF$_2$O; −140.3, −144.8, −146.0: OCF$_2$CF(CF$_3$)O.

Anal. Calcd. for CF$_3$O[CF$_2$CF(CF$_3$)OCF$_2$CF(CF$_3$)OCF$_2$O]$_n$CF$_2$CF$_3$: C, 21.02; F, 67.02. Found. C, 21.08; F, 67.08.

EXAMPLE 39

A mixture of 600 g 1,5-pentanediol and 30 g potassium hydroxide was heated to 160° C. in a 1 liter flask. Acetylene gas was bubbled through the solution as it was rapidly stirred. The reaction was stopped after 40 hours and the product was washed with water and distilled to give an 85% yield of pentanediol divinyl ether (b.p. 192° C.).

A 1 liter flask cooled to −12° C. was charged with 104 g pentanediol and a trace of methane sulfonic acid. To this solution was added 156 g pentanediol divinyl ether. The solution was stirred rapidly for 2 hours. Then slowly warmed to room temperature over a 6 hour period to give a viscous polymer having viscosity of 650 cst. at 100° F.

The product from the above reaction was fluorinated in a liquid phase reactor containing 1,1,2-trichlorotrifluoroethane and a sufficient amount of fluorine to complex with all of the hydrogen fluoride formed during the reaction. A perfluoropolyether (average molecular weight of 1800) having the following structure was obtained:

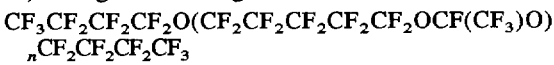

EXAMPLE 40

A mixture of 400 g triethylene glycol ethyl ether (2.24 mol), 258 g acetaldehyde diethylacetal (1.39 mol), 300 ml benzene and 10 g acidic ion exchange resin was refluxed in a 1 liter stirred flask equipped with a continuous extractor to remove the by-product ethanol from the refluxing benzene. The solution was refluxed for 6 hours, then filtered and placed in a rotary evaporator to remove the benzene solvent.

The product was fluorinated in a 22 liter stirred tank which contained 5.7 liters of 1,1,2-trichlorotrifluoroethane and 1100 g sodium fluoride powder. The hydrocarbon (219 g) was diluted to a volume of 700 ml with 1,1,2-trichlorotrifluoroethane. The solution was slowly pumped into the fluorination reactor, which was held at −5° C., over a period of 28 hours. The fluorine flow was set at a level approximately 10% higher than that required to react with all of the organic entering the reactor. Filtration of the crude reactor product followed by distillation yielded 224 g of a clear fluid which analyzed to be:

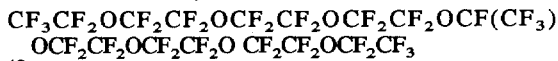

$^{19}$F NMR (δ ppm vs CFCl$_3$): −86.5: OCF(CF$_3$); −87.4: CF$_3$CF$_2$O; −88.0: CF$_3$CF$_2$O; −88.7: OCF$_2$CF$_2$O; −96.3: OCF(CF$_3$)O.

EXAMPLE 41

In an experiment very similar to the previous one, 400 g dipropylene glycol monomethylether (2.70 mol) was reacted with 159.5 g acetaldehyde diethylacetal (1.35 mol) in benzene with an acid catalyst. Fluorination of 250 g of the material afforded 480 g of a perfluorinated fluid having the following structure:

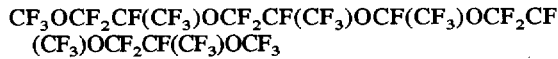

EXAMPLE 42

Chloroacetaldehyde (50 to 55 wt % in water) was distilled to give a fraction boiling between 87° and 92° C. A 3 liter stirred flask containing 1281 g of the chloroacetaldehyde distillate was placed in a room temperature water bath. While maintaining a temperature below 55° C., 500 ml of concentrated sulfuric acid was slowly added over a one hour period. The mixture was stirred for an additional 3 days at 53° C., then allowed to separate into two phases. The lower phase, containing sulfuric acid, was removed with a separatory funnel while the upper phase was placed into a 3 liter flask equipped with a mechanical stirrer. Concentrated sulfuric acid (200 ml) was carefully added to the solution while the temperature was held below 60° C. with a water bath throughout the addition. The flask was held at 50° C. for an additional 20 hours resulting in a viscous oil being formed. The polymeric product was dissolved in 1 liter methylene chloride and the solution was washed with water several times followed by a rinse with dilute sodium bicarbonate solution. The organic phase was isolated, dried over magnesium sulfate and concentrated to give a dark, viscous product (719 g polychloroacetaldehyde). The product was dissolved in 450 g chloroform and 305 g 1,1,2-trichlorotrifluoroethane to give a solution which was metered over a 22 hour period into a 20° C. fluorination reactor containing 5.5 liters of 1,1,2-trichlorotrifluoroethane. Following the reaction, the solvent was removed leaving behind a fluid with the following structure having an average molecular weight of 850:

$$[CFO]_n$$
$$|$$
$$CF_2Cl$$

| Temp. °F. | Viscosity (cst.) |
| --- | --- |
| −65 | 1240 |
| 100 | 2.53 |
| 176 | 1.14 |

EXAMPLE 43

Butoxyethoxyethanol (400 g, 2.47 mol) was reacted with 130 g polymeric chloroacetaldehyde in 150 ml benzene to give a fluid which distilled at 190° C. at approximately 1 torr. The product (266 g) was mixed with 500 ml 1,1,2-trichlorotrifluoroethane and pumped into a 15 liter fluorination reactor containing 5.7 liters 1,1,2-trichlorotrifluoroethane and 1150 g sodium fluoride powder. Fluorine, diluted with approximately four volumes of nitrogen, was metered into the 0° C. reactor at a rate approximately 10% greater than that required to react stoichiometrically with the polyether. The organic feed race was set to alloy complete addition in approximately 23 hours. Filtration of the product and removal of the 1,1,2-trichlorotrifluoroethane via a distillation gave a fluorocarbon product which was further purified by a 12 hour fluorination at 200° C. with 40% fluorine. Approximately 520 g of fluid was recovered with approximately 50% being the target material.

$$CF_3CF_2CF_2CF_2OCF_2CF_2OCF_2CF_2OCF(CF_2Cl)$$
$$OCF_2CF_2OCF_2CF_2O\ CF_2CF_2CF_2CF_3$$
b.p. 245.5° C.

$^{19}$F NMR (δ ppm vs CFCl$_3$) −73.3: OCF(CF$_2$Cl)O; −81.7: CF$_3$CF$_2$CF$_2$CF$_2$O; −83.3: CF$_3$CF$_2$CF$_2$CF$_2$O; −88.0 and −88.7: OCF$_2$CF$_2$O; −96.7: OCF(CF$_2$Cl)O: −126.5: CF$_3$CF$_2$CF$_2$CF$_2$O.

EXAMPLE 44

Chloroacetaldehyde dimethyl acetal (124 g, 1 mol), 1,3-dichloro-2-propanol (258 g, 2 mol) and 5 g ion exchange resin were mixed in a 1 liter stirred flask. The mixture was heated to allow the methanol formed in the reaction to slowly distill from the flask. Approximately 70 ml of methanol was recovered over a 6 hour period. The remaining solution was vacuum-distilled and the fraction (120 g, 38% yield) boiling between 100° C. and 145° C. at 2 mm Hg was collected. The fluid was shown by $^{19}$F NMR and elemental analysis to have the following structure:

$$(ClCH_2)_2CHOCHOCH(CH_2Cl)_2$$
$$|$$
$$CH_2Cl$$

The above acetal (210 g) diluted with a small amount of chloroform and 1,1,2-trichlorotrifluoroethane was metered over a 14 hour period into a 22° C. fluorination reactor containing 5.7 liters of 1,1,2-trichlorotrifluoroethane. The crude product was further treated with 30% fluorine at 200° C. for several hours to give 197 g (57% yield) of clear fluid:

$$(CF_2Cl)_2CFOCFOCF(CF_2Cl)_2$$
$$|$$
$$CF_2Cl$$

b.p.: 202° C.

$^{19}$F NMR (δ ppm vs CFCl$_3$): −64.5 and −65.0(a), −71.0 (d), −86.7(c) and −133.7(b)

[(ClCF$_2$)$_2$CFO]$_2$ CF(CF$_2$Cl)
 a    b    c    d

EXAMPLE 45

Into a 1 liter stirred flask containing 300 ml benzene were placed 516 g 1,3-dichloro-2-propanol (4 mol), 120 g paraformaldehyde (4 mol) and 10 g ion exchange resin. The mixture was refluxed as the water formed during the reaction was continuously removed. After refluxing for 6 hours, the reaction mixture was filtered and vacuum-distilled to give 354 g of a product with the following structure:

(ClCH$_2$)$_2$CHOCH$_2$OCH(CH$_2$Cl)$_2$
b.p.: 141° C./0.05 mm Hg.

The above acetal (354 g) was mixed with 70 g chloroform and 360 g 1,1,2-trichlorotrifluoroethane and fluorinated over a 24 hour period at 20° C. using the procedure described in the previous example. The reaction product was concentrated and the crude product was further treated with fluorine at 200° C. to give 430 g of a clear fluid (69% yield) having a boiling point of 178° C.

$^{19}$F NMR (Δ ppm vs CFCl$_3$): −45.5(c), −65.3(a) and −137.1(b)

[(ClCF$_2$)$_2$CFO]$_2$ CF$_2$
 a    b    c

EXAMPLE 46

A mixture of 600 ml ethoxyethanol, 200 g epichlorohydrin and 10 g ion exchange resin was heated to 130° C. for 20 hours. The reaction mixture was then cooled, filtered and distilled to give 250 g of product which was then reacted with 116 g paraformaldehyde to give 266 g of a product boiling above 150° C. at 0.01 mm Hg.

Fluorination of 261 g of the product in a reactor containing 5 liters of 1,1,2-trichlorotrifluoroethane and 1000 g sodium fluoride gave 446 g of perfluorinated fluid of which approximately 70% had the following structure:

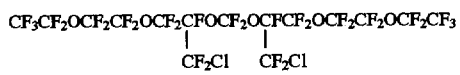

b.p. 224° C.

$^{19}$F NMR (δ ppm vs CFCl$_3$): −46.4(h), −67.6(g), −80.9(e), −87.6(a), −89.0(b,c,d), and −141.8(f)

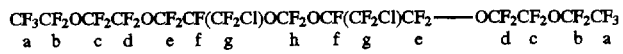

EXAMPLE 47

A mixture consisting of 100 g 2-chloroethanol (12.4 mol), 573 g epichlorohydrin (6.2 mol) and 20 g of an acidic ion exchange resin was refluxed for 24 hours. The mixture was then filtered to remove the ion exchange resin and the excess alcohol and unreacted epichlorohydrin were removed by distillation. The residue was distilled under vacuum and the product 1-chloro-3-(2-chloroethoxy)-2-propanol (804 g, 75% yield) distilled between 89° and 91° C. at 0.05 mm Hg.

Into a 1-liter stirred flask were placed 346 g 1-chloro-3-(2-chloroethoxy)-2-propanol (2 mol), 90 g paraformaldehyde (3 mol), 10 g ion exchange resin and 300 ml benzene. The mixture was refluxed for four hours as the water formed during the reaction was removed. The reaction mixture was filtered and distilled to give 267 g of a product (75% yield) with the following structure:

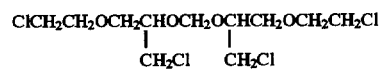

Fluorination of the product (660 g) in a typical reaction at 20° C. gave 1086 g of a product (82% yield) having the following structure:

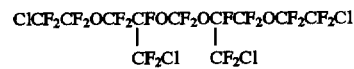

b.p.: 223° C.

$^{19}$F NMR: (δ ppm vs CFCl$_3$): −46.3(f), −67.3(e), −74.3(a), −81.0(c), −87.3(b) and −141.9(d)

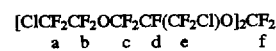

EXAMPLE 48

Into a 1 liter flask were charged 300 g trichloropentaerythritol, (1.58 mol), 150 ml of benzene, 10 g ion exchange resin and 60 g paraformaldehyde (2 mol). The mixture was refluxed as water was being removed continuously.

A portion of the above product, 192 g, was diluted with 1,1,2-trichlorotrifluoroethane to give 210 ml of solution which was pumped into a 22° C. reactor containing 4.3 liters of 1,1,2-trichlorotrifluoroethane. The reaction was complete in approximately 8 hours. The unreacted fluorine was flushed from the reactor with nitrogen gas and the product (307 g, 87.8% yield) was recovered by distillation:

$^{19}$F NMR (δ ppm vs CFCl$_3$): −48.9(e), −51.1(c), −66.4(b)

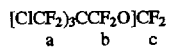

EXAMPLE 49

A mixture of 392 g 1,4 cyclohexanedimethanol (2.72 mol), 140 g paraformaldehyde (4.7 mol), 200 ml benzene and 10 g of a H$^+$ ion exchange resin was refluxed for several hours in a flask containing a water separator. A nearly quantitative yield of a sticky solid was obtained after removal of the solvent by distillation.

Fluorination of 263 g of the polymer, diluted with 220 g chloroform and 340 g 1,1,2-trichlorotrifluoroethane in a reactor (10° C.) containing 4.8 liters 1,1,2-trichlorotrifluoroethane and 1300 g sodium fluoride power, gave 440 g of a perfluoropolyether having the following structure:

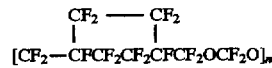

EXAMPLE 50

Into a 1 liter flask were placed 350 g tetraethylene glycol (1.8 mol), 300 ml benzene, and 10 g ion exchange resin. The mixture was refluxed for 1 hour to remove any moisture present. To the mixture was added 200 ml dimethoxypropane. The distillate was continuously removed over a 2-hour period in 50 ml increments, which were extracted with water to remove the ethanol formed in the reaction. After drying, the distillate was returned to the flask. An additional 200 ml dimethoxypropane was added and the distillate was collected, extracted, dried, and returned to the flask for an additional 3 hours. Removal of the resin and solvent yielded 410 g of a polymeric fluid having a viscosity of 360 cst. at 30° C.

Fluorination of 336 grams of the polyether in a 10° C. reactor containing 5 liters of 1,1,2-trichlorotrifluoroethane and 1420 g sodium fluoride powder gave 642 g of a perfluoropolyether having an average molecular weight of 1700 (69.8% yield).

$^{19}$F NMR: (δ ppm vs CFCl$_3$): −55.8(a), −76.3(e), −87.3(d), −88.6(c) and −90.5(b)

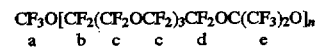

EXAMPLE 51

A mixture of 300 g pentanediol (2.88 mol), 450 g chloroacetaldehyde/water mixture having a boiling point between 87° and 92° C. and 150 ml benzene was refluxed in a flask containing a water separator. Approximately 5 grams of an acidic ion exchange resin was added to catalyze the reaction. After refluxing for approximately five hours the solution was filtered and the benzene was removed by distillation to leave a residue (approximately 400 g) having a viscosity of 9,700 cst. at 100° F.

Fluorination of 318 g of the polymer, diluted with 235 g chloroform and 375 g 1,1,2-trichlorotrifluoroethane, in a 12° C. reactor containing 5 liters of 1,1,2-trichlorotrifluoroethane and 1200 g sodium fluoride powder gave 623 g (84% yield) of the fluorinated polyether (average molecular weight of 2100) in a 22-hour reaction.

$^{19}$F NMR (δ ppm vs CFCl$_3$): −73.4(h), −74.3(e), −81.6(a), −82.3(d), −87.1(g), −122.1(f), −125.3(e) and −126.3(b)

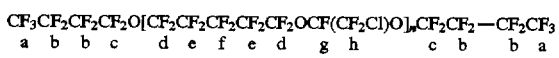
CF$_3$CF$_2$CF$_2$CF$_2$O[CF$_2$CF$_2$CF$_2$CF$_2$CF$_2$OCF(CF$_2$Cl)O]$_n$CF$_2$CF$_2$—CF$_2$CF$_3$
  a  b  b  c    d  e  f  e  d  g  h        c   b   b   a

EXAMPLE 52

A ten-liter stirred tank reactor was filled with 5.5 liters 1,1,2-trichlorotrifluoroethane. 220.3 grams of phenanthrene was placed in a one-liter brass tube fitted with a plug of copper turnings in each end of the tube and then filled with 1,1,2-trichlorotrifluoroethane. This brass tube was then placed in the liquid return line of the condenser so that the 1,1,2-trichlorotrifluoroethane condensed in the condenser would flow through the brass tube and dissolve some phenanthrene before entering the reactor. The fluorine flow was set at 470 cc/min and the nitrogen flow was set at two liters per minute. The reactor temperature and the brass tube containing the phenanthrene were both held at 19° C. during the reaction. After 20 hours, the fluorine was stopped and the reactor was dumped. In the brass tube, 21.8 grams of phenanthrene remained so a total of 198.5 grams had reacted.

From the reactor, after removal of the 1,1,2-trichlorotrifluoroethane, a pale yellow liquid was recovered. This material was then reacted with 40 cc/min fluorine and 100 cc/min nitrogen in an unstirred reactor where the fluorine was bubbled through the liquid at 200° C. for 12 hours to give a clear, colorless liquid. This liquid was then distilled to give 517 g (74.2%) of perfluorotetradecahydrophenanthrene (b.p. 215° C.) along with 128 grams of a clear, colorless solid that melted at approximately 60° C. and was much less volatile than the perfluorotetradecahydrophenanthrene.

EXAMPLE 53

5.3 liters 1,1,2-trichlorotrifluoroethane were placed in a ten-liter stirred tank reactor. 256 grams of kerosene was diluted to 650 ml with 1,1,2-trichlorotrifluoroethane. The fluorine flow was set at 650 cc/min with the nitrogen flow at 2 liters per minute. After three minutes the kerosene solution was added at 25 ml/hr to the reactor and the reaction was continued under these conditions while holding the reactor temperature at about 10° C. After 26 hours, all of the kerosene had been added and the fluorine flow was stopped fifteen minutes later. The product was distilled to remove the 1,1,2-trichlorotrifluoroethane and any other material with a boiling point below about 100° C. 575 grams of a clear, colorless liquid product was obtained after treatment with 30 cc/min fluorine and 60 cc/min N$_2$ at 150° C. for 15 hours.

EXAMPLE 54

A ten-liter stirred tank reactor was loaded with 3.3 liters 1,1,2-trichlorotrifluoroethane. 120 grams of heavy mineral oil was diluted to 480 ml with 1,1,2-trichlorotrifluoroethane. The fluorine flow was set at 350 cc/min with a nitrogen flow of 1.5 liters per minute. The mineral oil was added to the reactor at a rate of 20 ml/hr. After 24 hours, the reaction was complete and the reactor was dumped. After removal of the 1,1,2-trichlorotrifluoroethane, 385 grams of product was obtained. This product was then treated with 30 cc/min fluorine and 60 cc/min nitrogen at 200° C. for 16 hours to give 306 grams of a soft paste that became a completely clear, colorless liquid at approximately 80° C.

EXAMPLE 55

A ten-liter stirred tank reactor was loaded with five liters of 1,1,2-trichlorotrifluoroethane. 202 grams of Amoco Indopol™ H-100 polybutene (MW 920) was diluted to 610 ml with 1,1,2-trichlorotrifluoroethane. The fluorine flow was set at 460 cc/min with a nitrogen flow of 1.5 liters per minute. The polybutene was then added at a rate of 25 ml/hr while the reactor was held at −3° C. Once all the polybutene had been added (24 hours), the fluorine was reduced to 300 cc/min and the nitrogen reduced to 1.2 liters per minute and these conditions were maintained for 15 minutes after which the fluorine flow was stopped and the reactor was dumped. After removal of the 1,1,2-trichlorotrifluoroethane, the product was placed in a 600 ml beaker on a has plate in a fume hood for eight hours at approximately 120° C. to remove any light fraction in the oil. 496 grams of a viscous, colorless, slippery oil was obtained that has a pour point of about −15° C. and an average molecular weight of 1500.

EXAMPLE 56

A ten-liter stirred tank reactor was loaded with 5.0 liters 1,1,2-trichlorotrifluoroethane. 216 grams of Uniroyal Chemical's Trilene™ CP80 ethylene propylene copolymer (molecular weight approximately 8000) was diluted in 1,1,2-trichlorotrifluoroethane to give 800 ml. The fluorine flow was started at 420 cc/min and the nitrogen flow was at 1.6 liters/minute. After a few minutes, the CP80 solution was added at 25 ml/hr while the reactor was held at 10° C. After 31 hours, all of the CP80 solution had been added but the fluorine concentration in the gas outlet line rose only slowly. After one hour, the fluorine flow was reduced to 200 cc/min with a nitrogen flow of 800 cc/min and the conditions were held for five hours after which time the fluorine flow was stopped. When the reactor was dumped, a gelatinous product was obtained that was insoluble in the 1,1,2-trichlorotrifluoroethane. When all of the 1,1,2-trichlorotrifluoroethane was removed from the gelatinous product, 680 grams of somewhat brittle white solid was left. A small portion of this solid was ground into a powder and 20 grams was placed in a one-foot-long copper boat. This copper boat was placed in 1"×18" nickel cube and exposed to pure fluorine at 85° C. for 20 hours (5 cc/min F$_2$ flow). When this was done there was 20.6 grams of a very viscous, clear, colorless elastomer in the boat which was insoluble in 1,1,2-trichlorotrifluoroethane and all other solvents tried.

EXAMPLE 57

A ten-liter stirred tank reactor was loaded with 5.0 liters 1,1,2-trichlorotrifluoroethane. 275 grams of poly(alpha-methylstyrene) (having an average molecular weight of 685) was dissolved in 400 g chloroform and 400 g 1,1,2-trichlorotrifluoroethane to give about 800 ml. The fluorine flow was set at 350 cc/min and the nitrogen flow was set at 1400 cc/min. The poly(alpha-methylstyrene) solution was added at a rate of 20 ml/hr while the reactor temperature was held at 12° C. After 39 hours, all of the poly-(alpha-methylstyrene) solution had been added and the fluorine flow was left on for one more hour. When the reactor was dumped, a pale yellow solution, was recovered which contained approximately one gram of insoluble white powder.

The solution was filtered and the 1,1,2-trichlorotrifluoroethane was removed by distillation to give 785 grams of a pale yellow, somewhat brittle solid that melted at about 50° C. The melting point of the solid could be raised by distilling some of the low molecular weight product out of the solid. Approximately one third of the product boiled below 175° C. at 1 torr.

EXAMPLE 58

3.7 liters 1,1,2-trichlorotrifluoroethane were placed in a ten-liter stirred tank reactor. 69 g tri-n-hexylamine and 54 g trifluoroacetic acid were diluted in 1,1,2-trichlorotrifluoroethane to give 300 ml. The fluorine flow was set at 400 cc/min and the nitrogen flow was set at 1600 cc/min. The trihexylamine was added at 35 ml/hr while the reactor was maintained at 22° C. When all of the amine had been added (8 hours), the fluorine flow was reduced to 100 cc/min with the nitrogen at 800 cc/min. These conditions were maintained for four hours after which time the fluorine was turned off and the reactor was dumped. The product consisted of a colorless liquid with a thick, brown tar floating on top and coating the walls of the reactor. The soluble phase contained 71 grams of perfluorotrihexylamine (37%).

EXAMPLE 59

Into a 1 liter stirred flask were placed 350 g 1,5 pentanediol (3.4 mol), 23 g n-butanol (0.3 mol), 175 g paraformaldehyde (5.8 mol) and 200 ml benzene. Upon refluxing the mixture for approximately 3 hours with an acid catalyst present, 390 g of a polymeric fluid was obtained which had a viscosity of 450 cst. at 100° F. Fluorination of 310 g of the fluid in a typical fluorination reaction at 14° C. gave 708 g of fluid (80% yield) of which approximately 30% boiled between 200° and 300° C. at 0.05 mm Hg. The average molecular weight was 2800.

$^{19}$F NMR (δ ppm vs CFCl$_3$) −51.3(g), −55.7(c), −81.7(a), −85.0(d), −122.3(f), −125.5(e) and −126.7(b)

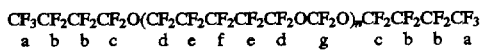

EXAMPLE 60

Using techniques similar to chose described in the previous examples, 350 g 1,6-hexanediol (3.0 mol) 49.3 g n-pentanol (0.56 mol), 134 g paraformaldehyde (4.46 mol) were reacted in benzene to give 425 g of a polymeric material having a viscosity of 600 cst. at 100° F. Fluorination of 628 g of the fluid in a typical reaction at 10° C. gave 628 g of fluid (71% yield), of which approximately 30% boiled between 200° and 300° C. at 0.05 mm Hg.

$^{19}$F NMR (δ ppm vs CFCl$_3$): −51.3(i), −56.0(b), −81.7(a), −85.0(f), −85.3(e), −122.7(h), −123.0(c), −125.5(g) and −126.3(d)

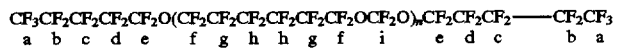

EXAMPLE 61

A mixture of 600 g diethylene glycol and 30 g potassium hydroxide was heated to 160° C. in a 1 liter flask. Acetylene gas was bubbled through the solution as it was rapidly stirred. The reaction was stopped after 48 hours and the product was extracted with water several times to remove any unreacted diethylene glycol. The product, a divinyl ether of diethylene glycol, was recovered by distillation (b.p. 196° C.) in about an 80% yield.

A 1 liter flask cooled to −10° C. was charged with 250 g triethylene glycol ethyl ether and a catalytic amount of methane sulfonic acid. To this solution was added slowly 100 g diethylene divinyl ether. Following the addition, the flask was slowly warmed to room temperature over a 3 hour period. The product was distilled to 150° C. at 0.05 mm Hg to remove any unreacted starting materials.

The product from the above reaction can be fluorinated at 20° C. using the procedures outlined in the previous liquid phase fluorination examples to give a perfluorinated fluid of the following structure:

CF$_3$CF$_2$O(CF$_2$CF$_2$O)$_3$CF(CF$_3$)O(CF$_2$CF$_2$O)$_2$CF(CF$_3$)O (CF$_2$CF$_2$O)$_3$CF$_2$CF$_3$

C$_{24}$F$_{50}$O$_{11}$ b.p. 300° C.

EXAMPLE 62

A mixture of 300 g 1-propanol (5.0 mol), 231 g epichlorohydrin and 10 g ion exchange resin was refluxed for 22 hours. The reaction mixture was then cooled, filtered and distilled to give 281 g of 1-chloro-3-propoxy-2-propanol (74% yield). Reaction of this product with paraformaldehyde (2.8 mol) gave 202 g of product (69% yield) having the following structure:

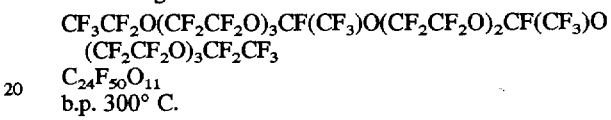

b.p.: 132° C. at 2 mm Hg.

Fluorination of the above acetal in a 23 hour reaction at 20° C. gave 404 g or product (81% yield) having the following structure:

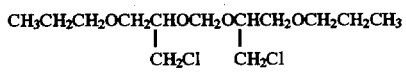

b.p.: 207° C.

$^{19}$F NMR (δ ppm vs CFCl$_3$): −46.3(g), −67.3(f), −80.4(d), −81.9(a), −84.5(c), −130.0(b) and −141.6(e)

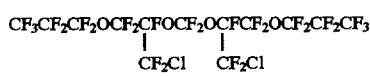

EXAMPLE 63

Eighty grams of diethoxymethane were fluorinated in a 4-liter stirred tank reactor containing 1.5 liters (CF$_2$Cl)$_2$CFOCF$_2$OCF(CF$_2$Cl)$_2$ as a fluorination solvent and 400 g sodium fluoride powder. The diethoxymethane, diluted with 200 ml of (CF$_2$Cl)$_2$CFOCF$_2$OCF(CF$_2$Cl)$_2$, was pumped into the reactor over an 18 hour period. Fluorination of the fluid at 10° C. with 30% fluorine gave a 90% yield of a product having a boiling point of 92.5° C. The product was obtained in greater than 99% purity following an atmospheric distillation.

$^{19}$F NMR (84.87 MHz, CFCl$_3$) –52.4 (pentet, c), –87.3 (singlet, a), –90.1 (triplet, b).

EXAMPLE 64

A mixture consisting of 500 g 2-chloroethanol (6.25 moles), 120 g paraformaldehyde (4 moles), 5 g of an acidic ion exchange resin and 100 ml benzene was refluxed for several hours. The water formed during the reaction was continuously removed. The mixture was filtered to remove the ion exchange resin and the unreacted 2-chloroethanol and benzene were removed by distillation. The residue was distilled to give bis(2-chloroethoxy)methane in a nearly quantitative yield. One hundred twenty grams of the product was fluorinated in a 4 liter stirred reactor containing 1.5 liters (CF$_2$Cl)$_2$CFOCF$_2$OCF(CF$_2$Cl)$_2$ in a 30 hour reaction at 20° C. to give a 92% yield of perfluoro[bis(2-chloroethoxy)methane]. The product (b.p. 92.5° C.) was obtained in greater than 99% yield by distillation.

$^{19}$F NMR (84.87 HHz, CFCl$_3$) –52.1 (pentet, c) –74.0 (singlet, a), –88.8 (triplet, b).

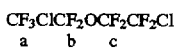

EXAMPLE 65

The reaction of 500 g dimethoxymethane (6.6 moles) with 100 g 1,3-dioxolane (1.4 moles), in the presence of an acidic catalyst, gave a mixture of unreacted dimethoxymethane, low molecular weight oligomers of 1,3-dioxolane and a product having the formula: CH$_3$OCH$_2$OCH$_2$CH$_2$OCH$_2$OCH$_3$ which was isolated in 50% yield. Fluorination of 80 g of the product in a 4 liter reactor containing 1.5 liters (CF$_2$Cl)$_2$CFOCF$_2$OCF(CF$_2$Cl)$_2$ and 400 g sodium fluoride in an 18 hour reaction at 10° C., gave a 60% yield of perfluoro-2,4,7,9-tetraoxadecane (b.p. 79.0° C.).

$^{19}$F NMR (84.87 MHz, CFCl$_3$) –54.1 (pentet, b) –57.7 (triplet, a), –90.9 (triplet, c).

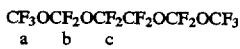

EXAMPLE 66

3,5,7-trioxanonane was prepared in low yield by reaction of 500 g ethanol (10.9 moles) with 500 g paraformaldehyde (16.7 moles) in 200 ml of benzene containing 5 g of an acidic ion exchange resin. The reaction was done in a 2 liter flask equipped with a water separator and reflux condenser. The major product formed, diethoxymethane, was removed from the product mixture along with the benzene by distillation. The remaining residue contained low molecular weight oligomers of formaldehyde having the general formula: CH$_3$CH$_2$(OCH$_2$)$_n$OCH$_2$CH$_3$. The primary component, CH$_3$CH$_2$OCH$_2$OCH$_2$OCH$_2$CH$_3$ was isolated in about a 10% yield. Fluorination of the product in (CF$_2$Cl)$_2$CFOCF$_2$OCF(CF$_2$Cl)$_2$ containing sodium fluoride gave a 45% yield of perfluoro-3,5,7-trioxanonane.

$^{19}$F NMR (84.87 MHz, CFCl$_3$–53.7 (multiplet, c) –87.4 (singlet, a). –90.6 (triplet, b).

EXAMPLE 67

Eighty grams of acetaldehyde diethyl acetal were fluorinated in 20 hour reaction using a fluorine flow rate of 250 cc/min. The hydrocarbon was slowly pumped into a reactor containing 1.5 liters (CF$_2$Cl)$_2$CFOCF$_2$OCF(CF$_2$Cl)$_2$ and 400 g sodium fluoride. The product, was obtained in a 45% yield and in 98% purity after distillation.

$^{19}$F NMR (84.87 MHz, CFCl$_3$) –86.7 (multiplet, d), –87.5 (singlet, a), –88.1 (multiplet, b), –97.0 (pentet, c).

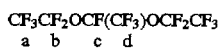

EXAMPLE 68

Eighty grams of triethyl orthoformate were fluorinated in a 4-liter stirred tank reactor containing 1.5 liters (CF$_2$Cl)$_2$CFOCF$_2$OCF(CF$_2$Cl)$_2$ and 400 g sodium fluoride powder. The triethyl ortho-formate, diluted with 200 ml (CF$_2$Cl)$_2$CFOCF$_2$OCF(CF$_2$Cl)$_2$ was pumped into the reactor over an 18 hour period. Fluorination of the fluid at 10° C. with 30% fluorine gave a 55% yield of a product having a boiling point of 92.5° C. The product was obtained in greater than 99% purity following an atmospheric distillation.

$^{19}$F NMR (84.87 HHz, CFCl$_3$) –52.2 (septet, c), –87.6 (singlet, a) –90.7 (doublet, b).

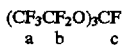

EXAMPLE 69

A mixture of 3,612 g butoxyethanol (30.6 moles), 261 g paraformaldehyde (8.7 moles), 5 g ion exchange resin and 350 ml toluene was stirred at reflux as the water formed in the reaction was continuously removed. After 5 hours, the reaction was complete and a nearly quantitative yield of bis(2-butoxyethoxy)methane, bp 100°–110° C. at 0.5 Torr, was recovered. 915 g of bis(2-butoxyethoxy)methane was diluted to a volume of 1700 ml with 1,1,2-trichlorotrifluoroethane and pumped into a 5 liter reactor containing 5.7 liters of 1,1,2-trichlorotrifluoroethane. The reaction, which was carried out at 23° C., was complete in approximately 72 hours. The product, perfluorobis(2-butoxyethoxy)methane was obtained in 62% yield.

$^{19}$F NMR (δ ppm vs CFCl$_3$) –51.7 (f), –81.6 (a), –83.4 c), –88.7 (e), –90.5 (d), –126.5 (b)

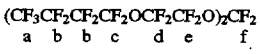

EXAMPLE 70

A 4 liter stirred reactor was charged with 2 liters Fluorinert FC-75 (3M Corporation; mixture of perfluoro(2-n-butyltetrahydrofuran) and perfluoro(2-n-propyltetrahydropyran)) and heated to 70° C. Eighty grams of bis(2-butoxyethoxy)methane was pumped into the reactor neat over an 18 hour period. The product, perfluorobis(2-butoxyethoxy)methane, was recovered in 41% yield following an atmospheric distillation (b.p. 178° C.). The $^{19}$F NMR was identical to that obtained when the product was prepared in 1,1,2-trichlorotrifluoroethane as the fluorination solvent (previous example).

EQUIVALENTS

Those skilled in the art will recognize or be able to ascertain using no more than routine experimentation many equivalents to the specific embodiments of the invention described herein. Such equivalents are intended to be encompassed by the following claims.

We claim:
1. A method for forming an essentially perfluorinated compound by liquid-phase fluorination in a reactor, comprising the steps of:
   a) introducing fluorine gas into an inert, liquid medium that is not the same as the essentially perfluorinated compound while forming an agitated medium, the fluorine gas being diluted so that the inert liquid medium and fluorine gas in a vapor space, which is formed above the liquid medium, do not form a flammable mixture;
   b) introducing a hydrogen-containing compound into the liquid medium so that the hydrogen-containing compound is dissolved or dispersed within the liquid medium;
   c) fluorinating until the hydrogen-containing compound is essentially perfluorinated, whereby the fluorine gas is introduced at a rate that is sufficient to remove the formed byproduct hydrogen fluoride from the reactor while under conditions which produce the essentially perfluorinated compound, wherein the fluorination reaction is carried out in the absence of a hydrogen fluoride scavenger under conditions including a temperature below the boiling point of the liquid medium but sufficiently high to allow byproduct hydrogen fluoride to be removed from the reactor, thereby forming the essentially perfluorinated compound; and
   d) removing the byproduct hydrogen fluoride from the reactor.

2. The method of claim 1 wherein the hydrogen-containing compound includes an ether or polyether having 5 to 10,000 carbon atoms.

3. The method of claim 1 wherein the liquid medium includes a perhalogenated chlorofluorocarbon.

4. The method of claim 3 wherein the perhalogenated chlorofluorocarbon includes 1,1,2-trichloro-trifluoroethane.

5. The method of claim 3 wherein the perhalogenated chlorofluorocarbon includes a perhalogenated chlorofluoropolyether.

6. The method of claim 1 wherein the hydrogen-containing compound is first dissolved in a solvent and is then introduced into the liquid medium in solution.

7. The method of claim 6 wherein the solvent does not consume fluorine.

8. The method of claim 7 wherein the solvent includes the same liquid as the liquid medium.

9. The method of claim 1 wherein the hydrogen-containing compound is insoluble in the inert, liquid medium and is introduced into the medium to form a suspension or emulsion.

10. The method of claim 9 wherein the emulsion or suspension is formed continuously in the reactor as the fluorination reaction proceeds.

11. The method of claim 1 wherein the liquid-phase fluorination is carried out at a temperature in a range of between about −40° C. and 150° C.

12. The method of claim 1 wherein the liquid-phase fluorination is carried out at a temperature in a range of between about −10° C. and 50° 1 C.

13. The method of claim 1 wherein the liquid-phase fluorination is carried out in a batch or continuous mode.

14. The method of claim 1 wherein the hydrogen-containing compound is extracted with liquid, perhalogenated chlorofluorocarbon or chlorofluoroether medium wherein the extracted hydrogen-containing compound is then fluorinated.

15. A liquid-phase process for forming an essentially perfluorinated organic compound, comprising the steps of:
   a) contacting in a temperature-controlled reactor a diluted solution or dispersion of a perfluorinateable, organic compound in a liquid, inert medium, said liquid, inert medium not being the same as the essentially perfluorinated organic compound, in the absence of a hydrogen fluoride scavenger with a stoichiometric excess of fluorine gas to essentially perfluorinate said organic compound at a temperature sufficient to volatilize the resulting byproduct hydrogen fluoride;
   b) removing said hydrogen fluoride from the reactor as it is produced; and
   c) removing separately from the reactor the resultant solution or dispersion of said perfluorinated organic compound.

16. A liquid-phase process for forming an essentially perfluorinated organic compound, comprising the steps of:
   a) introducing a perfluorinateable organic compound in the absence of a hydrogen fluoride scavenger into a temperature-controlled reactor having an agitated inert liquid medium to form a diluted solution or dispersion of the perfluorinateable, organic compound in the inert liquid medium, wherein said liquid medium is not the same as the essentially perfluorinated organic compound;
   b) introducing a stoichiometric excess of fluorine gas, while in the absence of a hydrogen fluoride scavenger, to perfluorinate said organic compound at a sufficient temperature and flow rate of the fluorine gas to volatilize and remove the resulting byproduct hydrogen fluoride from the reactor, thereby forming the essentially perfluorinated organic compound;
   c) removing said byproduct hydrogen fluoride from the reactor as it is produced; and
   d) removing separately from the reactor the resultant solution or dispersion of said perfluorinated organic compound.

17. The method of claim 16 wherein the gaseous products of the fluorination are circulated through a bed containing a hydrogen fluoride scavenger and then are reintroduced back into the temperature-controlled reactor.

18. A process for forming a perfluorinated organic compound, which yields hydrogen fluoride as a byproduct, comprising the steps of:
   a) providing a reaction system comprising a reactor and a means for conveying fluids through the reactor;
   b) conveying through the reactor a fluid comprising an organic compound, which can be perfluorinated to form the perfluorinated organic compound, and an inert liquid medium, said inert liquid medium not being the essentially perfluorinated organic compound;
   c) introducing fluorine gas into the fluid in the absence of a hydrogen fluoride scavenger, the ratio of organic compound to fluorine being sufficient to obtain a chemical reaction between them;

d) fluorinating the organic compound under turbulent conditions and for a time sufficient to yield the perfluorinated organic compound;

e) separating the byproduct hydrogen fluoride from the liquid phase comprising the inert, liquid medium and perfluorinated compound as both exit the reactor; and f) returning the liquid phase to the reactor.

19. The process of claim 18 wherein the fluorine gas is diluted with an inert gas.

20. The process of claim 19 wherein the inert gas includes nitrogen.

* * * * *